(12) United States Patent
Beyens

(10) Patent No.: US 10,466,145 B2
(45) Date of Patent: Nov. 5, 2019

(54) DIRECT ANALYSIS SAMPLER

(71) Applicant: HERAEUS ELECTRO-NITE INTERNATIONAL N.V., Houthalen (BE)

(72) Inventor: Dries Beyens, Kinrooi (BE)

(73) Assignee: HERAEUS ELECTRO-NITE INTERNATIONAL N.V., Houthalen (BE)

( * ) Notice: Subject to any disclaimer, the term of this patent is extended or adjusted under 35 U.S.C. 154(b) by 199 days.

(21) Appl. No.: 15/838,606

(22) Filed: Dec. 12, 2017

(65) Prior Publication Data

US 2018/0164193 A1 Jun. 14, 2018

(30) Foreign Application Priority Data

Dec. 13, 2016 (EP) .................................. 16203830

(51) Int. Cl.
| | | |
|---|---|---|
| *G01N 1/20* | (2006.01) | |
| *G01N 33/205* | (2019.01) | |
| *G01N 1/12* | (2006.01) | |

(52) U.S. Cl.
CPC ............. *G01N 1/20* (2013.01); *G01N 33/205* (2019.01)

(58) Field of Classification Search
CPC ......... G01N 1/20; G01N 33/205; G01N 1/125
USPC ...................................................... 73/863.71
See application file for complete search history.

(56) References Cited

U.S. PATENT DOCUMENTS

| | | |
|---|---|---|
| 3,455,164 A | 7/1969 | Boyle |
| 3,646,816 A | 3/1972 | Hance et al. |
| 4,037,478 A | 7/1977 | Cure |
| 4,120,204 A | 10/1978 | Cure |
| 4,125,024 A | 11/1978 | Vierbicky |
| 4,211,117 A | 7/1980 | Cure |
| 4,325,263 A | 4/1982 | Gaines, Jr. et al. |
| 4,361,053 A | 11/1982 | Jones et al. |
| 4,401,389 A | 8/1983 | Theuwis |
| 5,156,799 A | 10/1992 | Baerts |

(Continued)

FOREIGN PATENT DOCUMENTS

| | | |
|---|---|---|
| DE | 3344944 A1 | 6/1985 |
| FR | 2406822 A1 | 5/1979 |

(Continued)

OTHER PUBLICATIONS

European Search Report issued in EP Application No. 16203830.1 dated Jun. 16, 2017.

*Primary Examiner* — Nimeshkumar D Patel
*Assistant Examiner* — Jean F Morello
(74) *Attorney, Agent, or Firm* — Blank Rome LLP

(57) ABSTRACT

A sampler for taking samples from a molten metal bath, particularly a molten steel bath, includes a sample chamber assembly having a cover plate and a housing. The housing has first and second openings for an inflow conduit and a gas coupler, respectively. The first face of the housing includes a distribution zone, an analysis zone and a ventilation zone. A depth of the analysis zone is greater than 1.5 mm and less than 3 mm. The cover plate and the housing assemble together to form a sample cavity. An analysis surface of a solidified steel sample formed within the sample cavity lies in a first plane. In a flow direction of the molten steel, there are no increases in a width dimension of the sample cavity and a ratio of the length to depth of the sample cavity increases.

20 Claims, 11 Drawing Sheets

(56) References Cited

U.S. PATENT DOCUMENTS

| | | | |
|---|---|---|---|
| 5,415,052 A | 5/1995 | Baerts | |
| 9,128,013 B2 | 9/2015 | Song et al. | |
| 2014/0053647 A1* | 2/2014 | Beyens | G01N 1/125 |
| | | | 73/431 |
| 2014/0119404 A1* | 5/2014 | Beyens | G01N 27/411 |
| | | | 374/140 |
| 2014/0318276 A1 | 10/2014 | Cappa et al. | |
| 2017/0248499 A1* | 8/2017 | Pitts-Baggett | G01N 1/125 |
| 2018/0164191 A1* | 6/2018 | Beyens | G01N 21/69 |
| 2018/0164192 A1* | 6/2018 | Beyens | G01N 33/205 |
| 2018/0164195 A1* | 6/2018 | Beyens | G01N 1/12 |

FOREIGN PATENT DOCUMENTS

| | | |
|---|---|---|
| FR | 2413653 A1 | 7/1979 |
| JP | S52003487 A | 1/1977 |
| JP | S61199671 A | 9/1986 |
| JP | 2004012336 A | 1/2004 |
| RU | 2155948 C2 | 9/2000 |
| RU | 2508530 C2 | 2/2014 |
| RU | 2569417 C1 | 11/2015 |
| SU | 1161840 A1 | 6/1985 |

\* cited by examiner

DIRECT ANALYSIS SAMPLER

CROSS REFERENCE TO RELATED APPLICATION

This application claims the benefit of EP Application No. 16203830.1, filed Dec. 13, 2016, the contents of which are incorpoated by reference herein in its entirety.

TECHNICAL FIELD

The invention relates to a solidified sample of molten metal, particularly molten steel, which can be directly analyzed on an optical emission spectrometer.

BACKGROUND

During the processing of metals in their molten state, it is necessary to obtain a representative sample of the molten metal at various stages of the process, for example, for the analysis or evaluation of either the chemical composition or the metallographic structure of the metal sample. Different methods for analyzing molten metals (particularly steel) during manufacturing and further processing are known in the art. For example, German Patent No. DE 3344944 discloses a method for analyzing steel during its manufacture and further processing. The method is characterized by the following steps which are carried out consecutively: (1) magazineing a sampling lance and automatically pre-selecting the sample type; (2) collecting a sample of molten steel during the blowing phase in a converter or an electric furnace from a control stand; (3) unpacking the sampling lance and disposing of its cardboard and ceramic parts in an unpacking machine; (4) comparing the mass of the sample with a specified value for the purpose of early fault detection; (5) passing the sample through a cooling section supplied with water, air, inert gas and dry ice; (6) conveying the sample with the aid of a cartridge by means of a pneumatic tube conveyor section having an automatic sending and receiving station; (7) preparing the sample for spectral analysis in an automatic sample polishing machine; (8) detecting faults in the polished steel samples and documentation of the defects; (9) transferring the steel sample to the Petri stage of a spectrometer using a manipulator; (10) analyzing the sample in the spectrometer; and (11) communicating the analytical data to the control stand. In a typical steelmill, some of the above steps are manual and others robotic. However, the entire analytical process is time consuming and labor intensive.

Conventional sampling devices (e.g., the sampling lance of German Patent No. DE 3344944) to extract samples from a molten metal bath are also known from published patents and patent application. Other conventional sampling devices, which are not the subject of a patent or patent application, are known, for example, due to their availability on the market. These conventional sampling devices or samplers generally provide a coupon or disc of solid metal for use in spectrographic and metallographic analysis.

The geometric shape and dimensions of the solidified metal coupons obtained by such sampling devices will sometimes be specific to the type of metal or metallographic need. However, a general category of samples that are obtained by immersion devices are samples having a disc or oval shape and a diameter or long length of 28-40 mm. Most commonly, such samples have a diameter or long length of about 32 mm and a thickness of 4-12 mm. Some samplers, commonly known as lollipop samplers, may produce a differently shape sample, ranging from round to oval or longer, according to the requirements of the user, but most samples still have a diameter or long length of about 32 mm.

Other samplers, commonly known as dual thickness samplers, combine two thicknesses within the same sample. For analysis of the dual thickness samples, the 12 mm section is the portion which is spectrally analyzed. It has been found that a solidified sample of this thickness requires surface grinding from 0.8 to 5 mm in order to achieve an analysis surface which is free from metal and non-metallic segregation. Eliminating the need for surface preparation would speed the analysis time and would economically be favorable. However, this would only be achievable by a uniform filling of the sample cavity with molten metal and rapid chilling of the molten metal sample, such that the entire sample section freezes uniformly.

Typical sampling devices include a sample chamber or mold cavity configured to be filled with molten metal upon immersion of the sampling device into the molten metal bath. The molds which delineate the mold cavity or sampling chamber are typically either a two-part clam shell type arrangement or a ring covered on its upper and lower sides by flat plates. U.S. Pat. No. 3,646,816 describes this type of expendable immersion sampler, in which both flat surfaces of a disc-like sample are formed by chill-plates to achieve more rapid freezing and a pair of smoother surfaces which require less clean-up prior to analysis. Other prior art patents, such as U.S. Pat. No. 4,211,117, relate to a similar concept, while U.S. Pat. Nos. 4,401,389 and 5,415,052 provide examples of this metallurgical sample being combined with other sensors, one of which could be a temperature measuring sensor.

Historically, in all but a limited number of circumstances, the solidified metal sample obtained at a metallurgical process location is physically transported to a remote chemical laboratory, where the composition of the solidified metal sample is often determined using arc spark-optical emission spectroscopy equipment. Optical emission spectroscopy (or "OES") systems are generally the most effective systems for determining the chemical composition of a metal sample and for controlling the processing of molten metals due to their rapid analysis times and inherent accuracy. The results of this analysis are then returned to the metallurgical process location where the attending operators utilize those results to make decisions regarding further processing. Broadly speaking, the OES analysis procedure begins with the conductive metal sample being positioned with its analysis surface face down on a predetermined region of the stage of the OES instrument, namely an optical emission spectrometer. More particularly, the sample is positioned so as to span and close the analysis opening of the spectrometer and an anode nearly abuts the analysis surface of the sample. Once the desired positioning of the sample and proximity of the anode and analysis surface is achieved, a spark is discharged between the anode and the conductive metal sample which is electrically connected to the spectrometer stage. This connection is, in most cases, made by gravitational force in combination with a small load. The analysis opening on the optical emission spectrometer is typically around 12 mm wide. This distance avoids that a spark arcs between the anode and the instrument housing. The optical detector receives the emitted light from the excavated material of the sample surface. The spark chamber, formed in part by the space between the anode and the metal sample, is continuously purged with argon or other inert gas in order to avoid air ingress which would lead to erroneous analysis values.

In order to lay flat across the analysis opening of the spectrometer, the metal sample cannot have any extensions and the analysis surface of the metal sample must be smooth (i.e., of there can be no parts of the sample housing which break the plane of the analysis surface). The sample must span the analysis opening of the spectrometer and be of sufficient flatness to facilitate inert gas purging of the spark chamber and present a contiguous sample surface toward the anode.

It has been demonstrated that when placing such analytical equipment in a factory environment, near the metallurgical process location, more timely results are obtained and significant cost savings can be gained by eliminating transport and handling efforts. There are several problems associated with providing a metallurgical sample for these types of local analytical systems, as well as some prior art solutions for these problems. For example, it has been found that exposing the hot metal surface of the solidifying or solidified sample to atmosphere will quickly result in the formation of oxides on its surface, which must be later removed by mechanical grinding in order for the sample to be analyzed by OES. One solution to this problem has been to remove the heat of the solidifying metal to bring the metal sample to near room temperature before it is removed from the sample chamber.

Direct Analysis (DA) samplers are a newly developed type of molten metal immersion sampler which produce DA samples. DA samples do not require any kind of surface preparation before being analyzed, and thus can result in significant economic benefit both in terms of the availability of timely chemistry results as well as laboratory time savings by utilizing the OES analysis method.

U.S. Pat. No. 9,128,013 discloses a sampling device for retrieving a rapid chilled sample from a converter process for making steel that is intended for local analysis. The sampling device includes a sample chamber formed by at least two parts, where the specified ratio of the mass of the melt taken up in the sample cavity to the mass of the sample chamber assembly enables a rapid cooling of the melt filling the sample cavity. When this sample chamber is removed from the measuring probe, thereby exposing the sample surface to atmosphere, the melt has already cooled sufficiently that oxidation is prevented to the greatest extent possible, and therefore post-treatment of the sample surface is unnecessary.

A similar DA type sampler is known from U.S. Patent Application Publication No. 2014/318276. One end of the sample cavity of this DA type sampler is connected to the molten metal bath during immersion of the sampler via an inflow conduit, while an opposite end of the sample cavity is in communication with a coupling device. During immersion, but before the filling of the sample cavity with the molten metal, the sample cavity is purged with an inert gas to avoid early filling and oxidation of the sampled material. The inflow conduit is arranged perpendicular to the flat surface of the sample cavity. The ventilation of the sample cavity is arranged below the analysis surface of the sample cavity relative to the immersion direction.

The above-described sampling device is meant to be used in steelmaking processes, specifically in a converter application. Steel samples and steel bath temperatures are measured either from the tilted converter after interruption of the blow or by means of special equipment called a sublance, according to U.S. Patent Application Publication No. 2014/318276. In the latter case, the converter can stay upright and the blowing process can continue, thus saving time. The oxygen steelmaking process aims to achieve precise end point values for steel weight, temperature and composition. Carbon, phosphorus and sulphur concentration and, in some instances, special elements detrimental to the final steel properties are monitored for their content in the steel to be within compositional target windows. A fast analysis DA type sampler can provide the confirmation of the composition in much less time than a conventional sampling device, since the analytical procedure is reduced to de-molding the solidified sample, transferring the sample to a spectrometer and placing the sample on an OES stage for analysis.

In converter applications, the oxygen content of the steel is considered high. In particular, at the end of the oxygen blowing process, the oxygen content of the steel is typically on the order of 500-1000 ppm. A sample taken from this bath would cool and expel carbon monoxide when the decreasing temperature of the steel (i.e., during cooling) exceeds the oxygen solubility for that temperature and its carbon content. These gas bubbles lead to an irregular surface and a hollow sponge like structured sample. To avoid this problem during cooling, prior art samplers, such as those described in U.S. Pat. Nos. 4,037,478 and 4,120,204, are provided with a deoxidant, most commonly aluminum and zirconium. However, a rapidly filled DA sampler with a small cross section and rapid chill sample chamber has been shown to result in a poor distribution of the deoxidant as the section of the sample decreases, thus establishing a limitation to reduction of the sample volume.

Thus, there is a need to provide a means for mixing deoxidizing materials into rapid chill samplers to obtain an improved distribution.

Also, samples produced by conventional sampling devices have a diameter of at least 32 mm in a direction parallel to the spectrometer opening and a thickness of 4-12 mm in a direction perpendicular to the spectrometer opening. Such dimensions can be easily handled by pre-analysis preparation equipment that mechanically grinds the analysis surface of the metal sample to clean oxides from the surface and provide the requisite flat topography. This geometry is also convenient to robotic manipulators which advance the sample from preparation through analysis and removal to await the next sample. Robotic equipment in a typical steelworks laboratory is difficult to modify to accept radically different sample geometries.

However, the prior art sample volume is over dimensioned from the minimum volume of metal required to arrive at the minimum necessary analyzed surface area. The sample volumes of the prior art devices thus preclude rapid solidification of the molten metal sample, which is necessary to obtain an oxide free surface. As such, conventional devices cannot be reliably analyzed by OES without surface preparation. Using massive cooling plates and sampler housings to force a large volume metal sample to low temperature after retrieval becomes impractical for rapid de-molding and is uneconomical for use as immersion sampling devices.

Accordingly, it would be beneficial to provide a DA type sampler which produces preparation free samples of deoxidized steel from a converter or other processing vessel that are capable of rapid chilling as necessary for obtaining an analysis surface which is free from metal and non-metallic segregation which can be analyzed by OES.

It would also be beneficial to provide a DA type sampler, particularly one which is adaptable for use in sampling molten steel, which produces a DA type sample capable of being analyzed on existing OES equipment, thereby improving the speed and accuracy of the analysis.

It would also be beneficial to provide a molten metal immersion device for retrieving preparation free samples from a molten metal processing vessel which is capable of quick connection to pneumatic-assisted inert gas purge apparatus and exhibits reduced pressure metal uptake. In particular, it would be beneficial to provide a molten metal immersion device for producing a molten metal sample that is easily obtained and quickly removed from the immersion device housing, de-molded from the sample chamber, and directly analyzed on the OES without additional cooling or preparation, and which is thereby cost-effective.

SUMMARY

The invention relates to a rapid chilled sampler which is filled with molten metal in the immersion direction parallel to the longitudinal axis and which produces a locally analyzed metallurgical sample. This configuration, as described in more detailed herein, provides the greatest utility on existing optical emission spectrographs which, at present, require an analyzable surface to be of certain dimensions, and also provides an optimum geometry fitting into the aforementioned carrier tubes in order to remove and de-mold the metal sample with minimal effort.

In summary, the following embodiments are proposed as particularly preferred in the scope of the invention:

Embodiment 1

A sampler for taking samples from a molten metal bath, particularly a molten steel bath, the sampler comprising:
a carrier tube having an immersion end;
a sample chamber assembly arranged on the immersion end of the carrier tube, the sample chamber assembly comprising a cover plate and a housing,
characterized in that the housing includes:
an immersion end having a first opening for an inflow conduit and an opposing end having a second opening for a gas coupler,
a first face extending between the immersion end and the opposing end, the first face having a first depression proximate the immersion end and a second depression, the first depression being an analysis zone and the second depression being a ventilation zone, a portion of the analysis zone overlying a distribution zone which is in direct flow communication with the first opening and configured to receive the molten steel from the inflow conduit,
wherein a depth of the analysis zone is greater than 1.5 mm and less than 3 mm,
wherein the cover plate and the housing are configured to be assembled together to form a sample cavity including the distribution zone, the analysis zone and the ventilation zone, such that an analysis surface of a solidified steel sample formed within the sample cavity lies in a first plane,
wherein the first and second openings are spaced apart from the first plane.

Embodiment 2

A sampler according to the preceding embodiment, characterized in that the sample cavity and the first and second openings are aligned along a common longitudinal axis.

Embodiment 3

A sampler according to any of the preceding embodiments, characterized in that the analysis zone, distribution zone and ventilation zone are structured as a plurality of contiguous segments, each segment having a length to depth ratio, a sum of the length to depth ratios of the plurality of segments being greater than 25, preferably greater than 50.

Embodiment 4

A sampler according to any of the preceding claims, characterized in that the distribution zone, analysis zone and ventilation zone are structured as a plurality of contiguous segments, each segment having a length to depth ratio, the length to depth ratios of the segments successively increasing as the distance from the first opening increases.

Embodiment 5

A sampler according to any of the preceding embodiments, characterized in that there are no increases in a width dimension of at least a portion of the analysis zone, in a flow direction of the molten steel, which extends from the end of the distribution zone toward the second opening.

Embodiment 6

A sampler according to any of the preceding embodiments, characterized in that a total length of the analysis zone and the ventilation zone is between 20 and 50 mm, preferably 30 mm long.

Embodiment 7

A sampler according to any of the preceding embodiments, characterized in that the analysis zone has a uniform depth above the distribution zone.

Embodiment 8

A sampler according to any of the preceding embodiments, characterized in that a cross-sectional area of the analysis zone gradually tapers in the flow direction of the molten steel.

Embodiment 9

A sampler according to any of the preceding embodiments, characterized in that a cross-sectional area of the ventilation zone gradually tapers in the flow direction of the molten steel.

Embodiment 10

A sampler according to any of the preceding embodiments, characterized in that a ratio of a mass of the sample chamber to a mass of the metal received within the sample collection volume is 9 to 12, preferably 10.

Embodiment 11

A sampler according to any of the preceding embodiments, characterized in that the cover plate accounts for 10 to 20 percent of the mass of the sample chamber.

Embodiment 12

A sampler according to any of the preceding embodiments, characterized in that a cross-sectional area of the inflow conduit is between 0.20 and 0.70 times of a cross-sectional area of the distribution zone, preferably 0.55.

Embodiment 13

A sampler according to any of the preceding embodiments, characterized in that a bottom surface of the distribution zone intersects a closed bottom end of the analysis zone at an angle between 40° and 90°, preferably 60°.

Embodiment 14

A sampler according to any of the preceding embodiments, characterized in that the cover plate includes a gasket configured to provide a substantially gas tight seal between the cover plate and the housing.

Embodiment 15

A sampler according to any of the preceding embodiments, characterized in that the cover plate is secured to the housing by a metal clamp to form the sample chamber.

Embodiment 16

A sampler according to any of the preceding embodiments, characterized in that the first and second openings are the only openings formed in the sample cavity, an end of the inflow conduit being secured within the first opening and an end of the gas coupler being secured within the second opening.

Embodiment 17

A sampler according to any of the preceding embodiments, characterized in that a cross-sectional area of the inflow conduit is between 0.5 and 2 times of a cross-sectional area of the analysis zone.

Embodiment 18

A sampler according to any of the preceding embodiments, characterized in that the inflow conduit, the distribution zone, the analysis zone, the ventilation zone and the gas coupler are sequentially arranged in this order in the flow direction of the molten steel.

Embodiment 19

A sampler according to any of the preceding embodiments, characterized in that the first face of the housing includes a ridge protruding therefrom and surrounding the ventilation zone, the analysis zone and the distribution zone.

Embodiment 20

A sampler according to any of the preceding embodiments, characterized in that when the cover plate and the housing are assembled together, the cover plate sits flush against the ridge of the housing along the first plane.

BRIEF DESCRIPTION OF DRAWINGS

The foregoing summary, as well as the following detailed description of preferred embodiments of the invention, will be better understood when read in conjunction with the appended drawings. For the purpose of illustration, there are shown in the drawings embodiments which are preferred. It should be understood, however, that the device and method are not limited to the precise arrangements and instrumentalities shown.

DETAILED DESCRIPTION

The invention relates to an immersion sampling probe for producing a solidified strip sample of solidified steel for direct analysis by OES.

Figure 1:
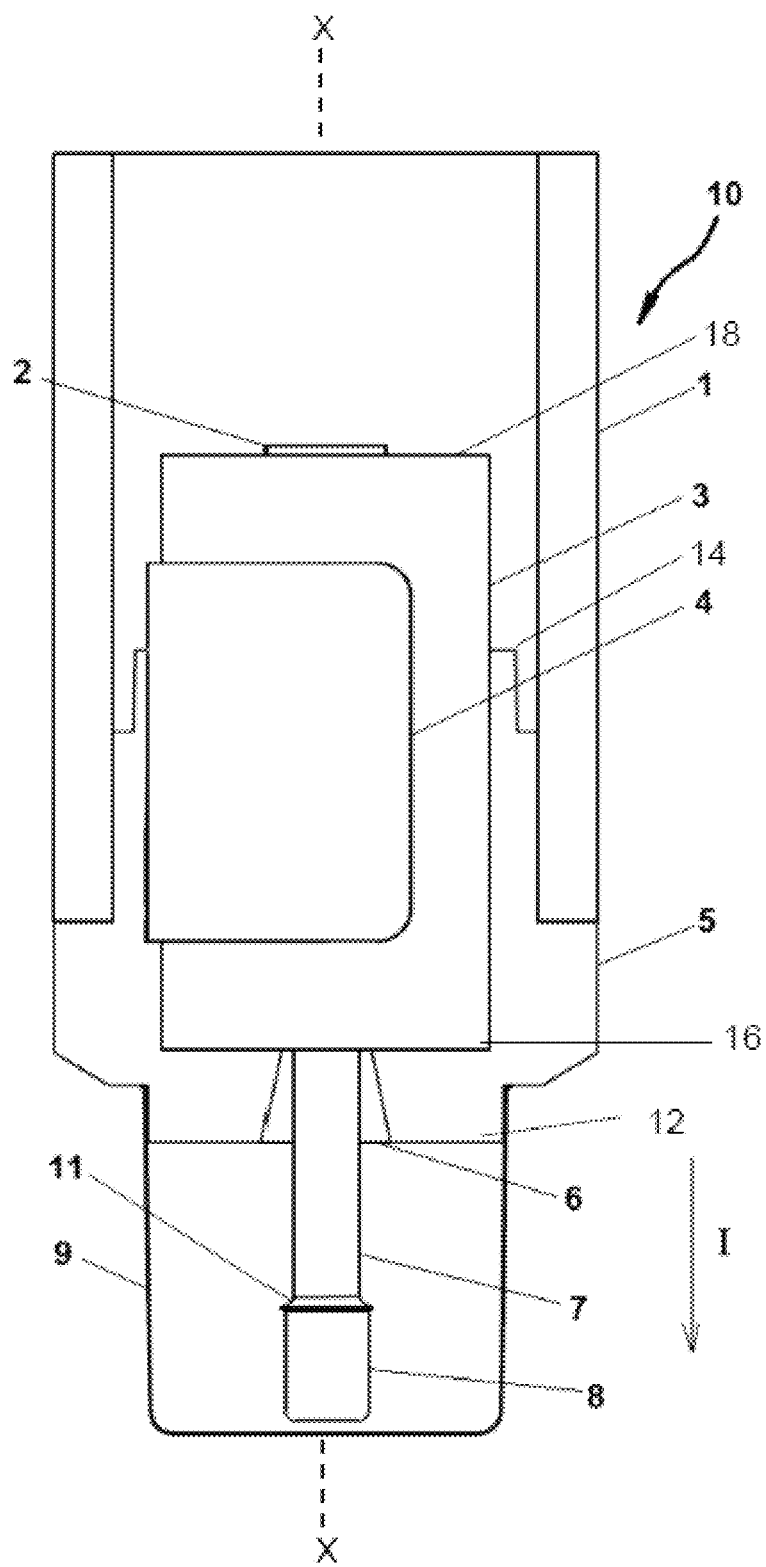
FIG. 1 is a side elevational view of an immersion sampling probe oriented in the immersion direction in accordance with one embodiment of the invention.

Referring to FIG. 1, there is shown an immersion sampling probe 10, and more particularly a molten metal sampling probe 10. Most preferably, the probe 10 is suitable for immersion in and sampling of molten steel. The probe 10 comprises a measuring head 5. The measuring head 5 is preferably made of resin bonded silica sand. However, it will be understood by those skilled in the art that the measuring head 5 may be made of any material known to be suitable for forming a body to be immersed in molten metal.

The measuring head 5 is supported on a carrier tube 1. Preferably, the carrier tube 1 is a paper carrier tube. In use, a probe holder or lance (not shown) is preferably inserted into the interior volume of the carrier tube 1 to provide the mechanical action necessary to submerse the measuring head 5 below the surface of a bath of molten metal (not shown) in the immersion direction I.

The measuring head 5 comprises a sampling chamber 3 for collection and retrieval of a sample of molten metal. It will be understood by those skilled in the art that while the sample chamber 3 is described herein in terms of the immersion sampling probe 10, the sample chamber 3 may be utilized with any type of molten metal sampling device. Thus, the assembly and configuration of the sample chamber 3 described herein is applicable to any type of molten metal sampling device, not just the immersion sampling probe 10.

Preferably, the sample chamber 3 is a two-part sampling chamber. More particularly, referring to FIG. 2, the sample chamber 3 is composed of a housing 30 and cover plate 32. The housing 30 is preferably formed of one or more materials which are good thermal and electrical conductors, such as, but not limited to, aluminum, copper and other metals having similar thermal and electrical conductivity properties for being electrically coupled to the retrieved metal sample. Preferably, the housing 30 is made of aluminum. The mass of the closing plate 32 preferably accounts for 10 to 20% of the overall mass of the sample chamber 3. The housing 30 may be marked by an indestructible method with identification means.

The two parts 30, 32 of the sample chamber 3 are preferably held together by a clamp 4 (also referred to as a clip) with a compression force sufficient to resist a tendency of the two parts 30, 32 of the sampling chamber 3 to separate due to the force of molten metal flowing into and filling the sample chamber 3. The clamp 4 is preferably a metal clamp. However, it will be understood by those skilled in the art that the clamp 4 may be made of another suitable material which is capable of immersion in molten metal and provides the requisite compressive force.

Referring to FIG. 1, the measuring head 5 has a first end 12 and an opposing second end 14. The first end 12 of the measuring head 5 corresponds to an immersion end. The second end 14 of the measuring head 5 is configured to face the lance or probe holder. The sample chamber 3 has a first end 16 and an opposing second end 18. The first end 16 of the sample chamber 3 corresponds to an immersion end. It will be understood by those skilled in the art that the phrase "immersion end" means the end of the body which is first immersed into molten metal in the immersion direction I.

The sample chamber 3 includes a sample cavity configured to receive molten metal, as described in greater detail herein. The sample cavity extends from proximate the first end 16 toward the second end 18 of the sample chamber 3 along a longitudinal axis X (see FIG. 4).

The first end 16 of the sample chamber 3 is preferably attached to or otherwise provided with an inflow conduit 7. More particularly, the first end 16 of the sample housing 30 has a first opening 20 for receiving the inflow conduit 7 (see FIG. 4). The first opening 20 and thus the inflow conduit 7 are preferably aligned with the sample chamber 3, and more particularly the sample cavity. The inflow conduit 7 enables the flow of molten metal from the molten metal bath into the sample chamber 3. Thus, molten metal is introduced into the sample cavity of the sample chamber 3 in the immersion direction parallel to the longitudinal axis X of the sample cavity. The inflow conduit 7 is preferably made of a quartz material, more preferably a fused quartz material. However, it will be understood that the inflow conduit 7 may be made of any other suitable material, including, but not limited to, a ceramic material.

Figure 4:
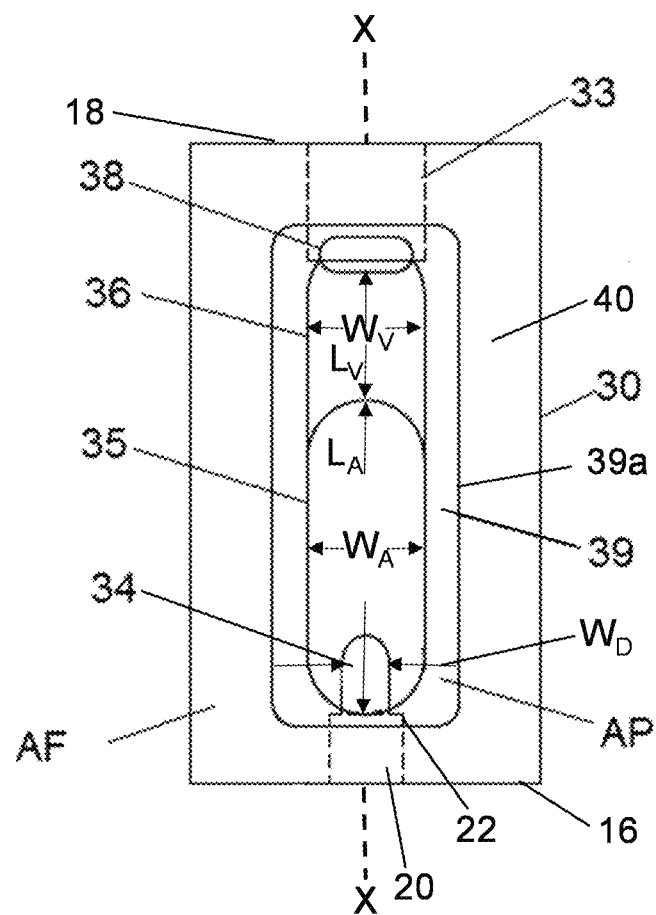
FIG. 4 is front elevational view of the housing of a two-part sample chamber of the immersion sampling probe of FIG. 1.
Figure 4A:
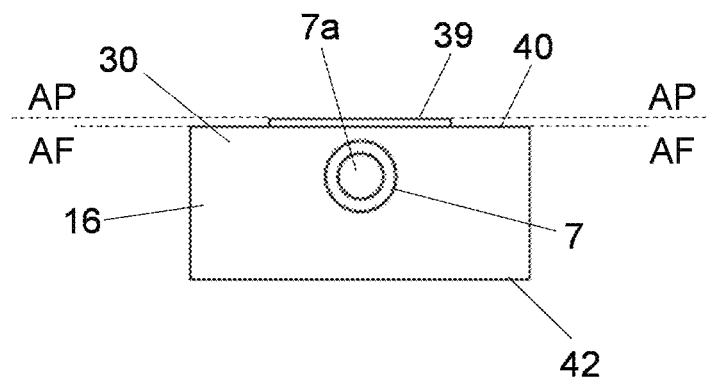
FIG. 4A is a bottom plan view of the sample chamber housing shown in FIG. 4.

The inflow conduit 7 has a first end (not shown) and an opposing second end 22 (see FIGS. 4-4A). In one embodiment, the inflow conduit 7 is secured within the measuring head 5 by a bushing 6 (see FIG. 1). The bushing 6 is preferably made of a cement material. The second end 22 of the inflow conduit 7 is adhered or attached within the sample chamber 3 by an adhesive 27 in a substantially gas tight manner. More particularly, the second end 22 of the inflow conduit 7 is positioned entirely within the first opening 20 of the housing 30 of the sample chamber 3 and is adhered therein by the adhesive 27 to achieve a substantially gas tight joint. "Substantially gas tight" means that the seal or joint may be completely gas tight or gas tight to a large degree. In particular, regarding the joining of the inflow conduit 7 and the gas coupler 2 (described herein), the joints formed are preferably gas tight to the extent that the sample cavity is capable of being pressurized above the pressure level at the immersion depth.

Figure 3:
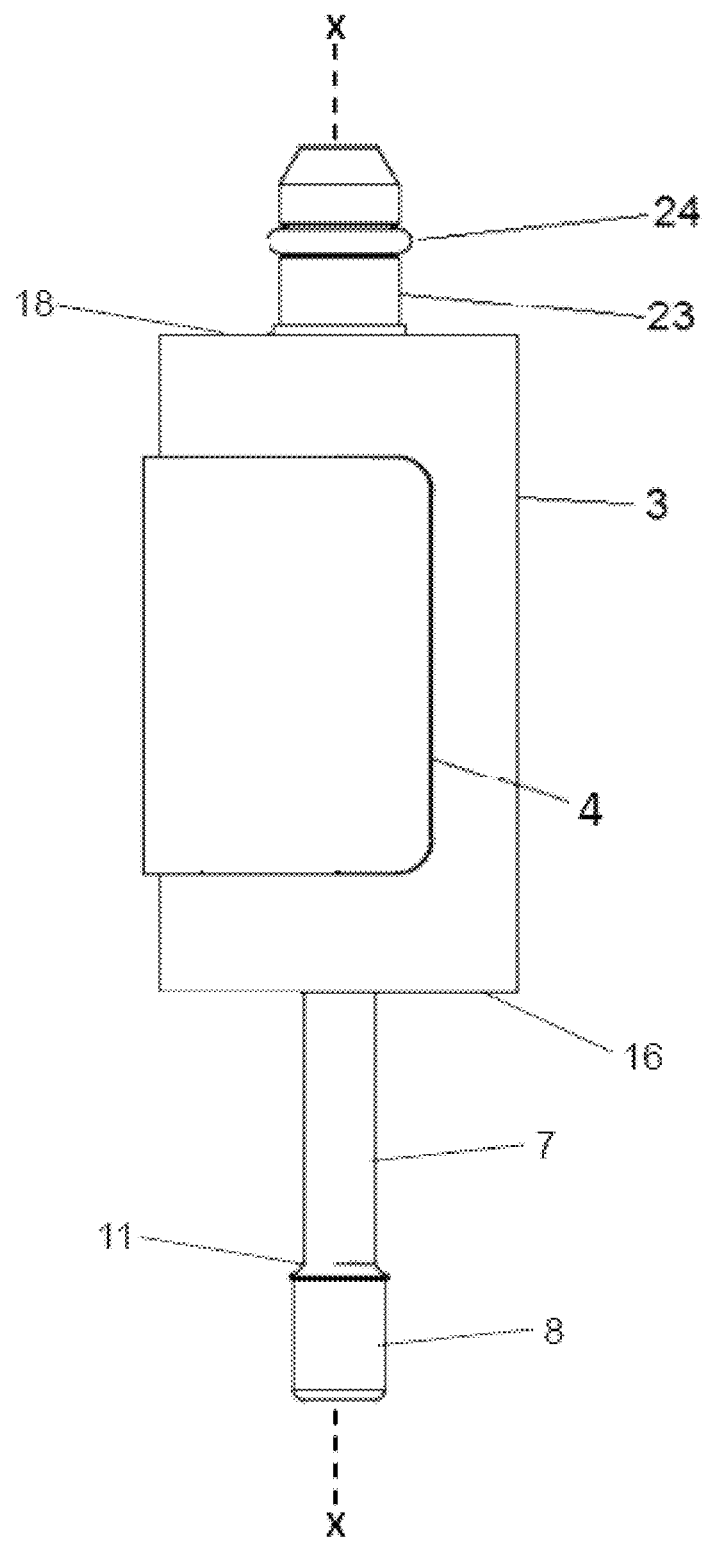
FIG. 3 is a side elevational view of the immersion sampling probe of FIG. 1 provided with a gas connector for connecting to a probe holder containing a pneumatic line.

Referring to FIGS. 1 and 3, the first end of the inflow conduit 7 corresponds to an immersion end. The first end is not visible on FIGS. 1 and 3, because it is covered by a first protection cap 8. More particularly, the first protection cap 8 is attached to the first end of the inflow conduit 7 in a substantially gas tight manner by adhesive 11. The first protection cap 8 is preferably made of metal, and more preferably steel. The first protection cap 8 may include an opening (not shown) (e.g., a 1 mm diameter hole) to ensure that the sample cavity can be sufficiently purged and that all entrapped air can be exhausted therefrom. A second protection cap 9, in turn, covers (and more specifically encompasses) the first protection cap 8. The second protection cap 9 is attached to the first end 12 of the measuring head 5. Preferably, the second protection cap 9 is made of metal, and more preferably steel. In one embodiment, the second protection cap 9 is further protected by a covering of paper (not shown).

Figure 2:
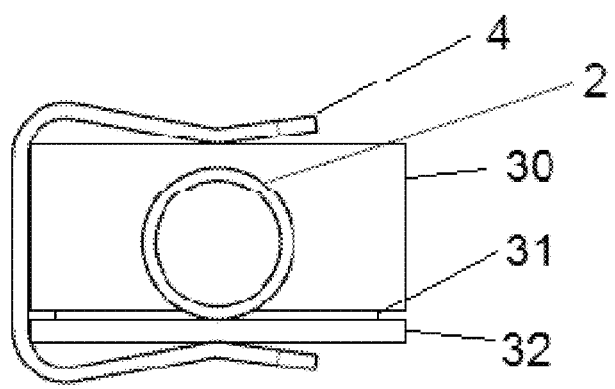
FIG. 2 is a top plan view of the immersion sampling probe of FIG. 1.

Referring to FIGS. 1-2 and 4, the second end 18 of the sample housing 30 includes a second opening 33 for receiving a coupler 2, and more particularly a gas coupler 2. The second opening 33 is thus a gas port which is preferably wholly contained within the housing 30. The coupler 2 is sealed to the housing 30 within the gas port 33 at the second end 18 of the sample chamber by an adhesive 26 to achieve a substantially gas tight joint. Thus, an end of the coupler 2 is positioned entirely within the body of the housing 30 of the sample chamber 3.

The coupler 2 is configured to mate with a conduit (not shown), and more particularly a gas conduit. More particularly, a first end of the gas conduit is attached to the coupler 2 and an opposing second end of the gas conduit is attached to a pneumatic system (not shown). The pneumatic system preferably supplies an inert gas to the sample chamber 3 via the gas conduit for purging and pressurizing the sample chamber 3. Examples of the inert gas which may be used to purge and pressurize the sample chamber 3 include, but are not limited to, nitrogen or argon. Preferably, the inert gas (e.g., nitrogen or argon) is at a pressure of 2 bar. The pneumatic system also facilities the removal of exhaust gases from the sample chamber 3 via the gas conduit. When a pneumatic system is in communication with the sampling chamber 3 of the probe 10 via the coupler 2, there is a continuous gas path from the immersion end of the inflow conduit 7 to the sampling chamber 3 (i.e., along the longitudinal axis X) that is substantially leak-free, yet the sample chamber 3 is easily disassembled in order to access the sample.

Referring to FIG. 3, in one embodiment, the coupler 2 is provided with a gas connector 23 configured to mate with a corresponding receptacle on the probe holder. More particularly, the gas connector 23 is a push-on/pull-off type of connector assembly and includes an O-ring 24 for gas sealing to a mating surface on the probe holder.

In use, the measuring head 5 is immersed into a molten metal bath and the sample chamber 3 is purged and pressurized by the inert gas which is supplied by the pneumatic system and which travels from the coupler 2 toward the inflow conduit 7 along the longitudinal axis X. After the measuring head 5 is immersed below the surface of the molten metal bath, the second protection cap 9 and the covering of paper (if present) melt due to the heat of the molten metal, thereby exposing the first protection cap 8 to the molten metal. Subsequently, the first protection cap 8 also melts, thereby placing the sample chamber 3 in fluid communication with the molten metal bath via the inflow conduit 7. More particularly, once the second protection cap 8 melts, the pressure of the inert gas exits from the sample chamber 3 via the open inflow conduit 7 (i.e., via the first end of the inflow conduit 7) until the pneumatic system reverses from a purge mode to an exhaust or vacuum mode. Molten metal then enters the sample chamber 3 through the inflow conduit 7, particularly from the first end to the second end 22 and subsequently into the sample cavity of the sample chamber 3, while gas is exhausted out of the sample chamber 3 through the coupler 2. The gas is preferably exhausted by the natural ferro-static pressure of the filling molten metal but may also be exhausted by a slight vacuum applied to the gas conduit by remote equipment.

Figure 5:
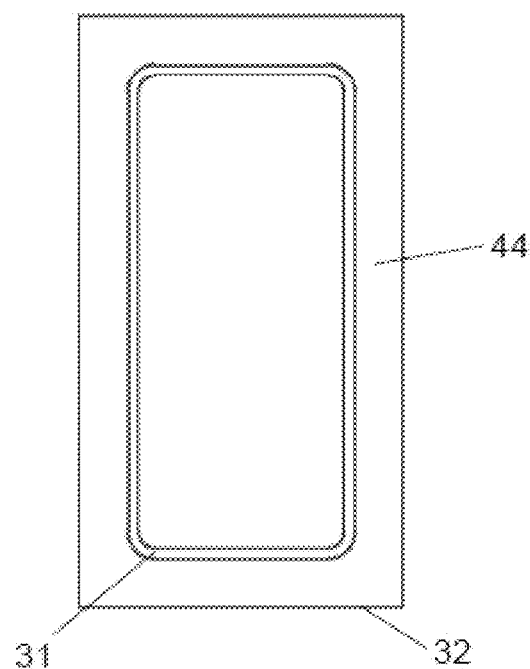
FIG. 5 is a front elevational view of the cover plate of the two-part sample chamber of the immersion sampling probe of FIG. 1.
Figure 6:
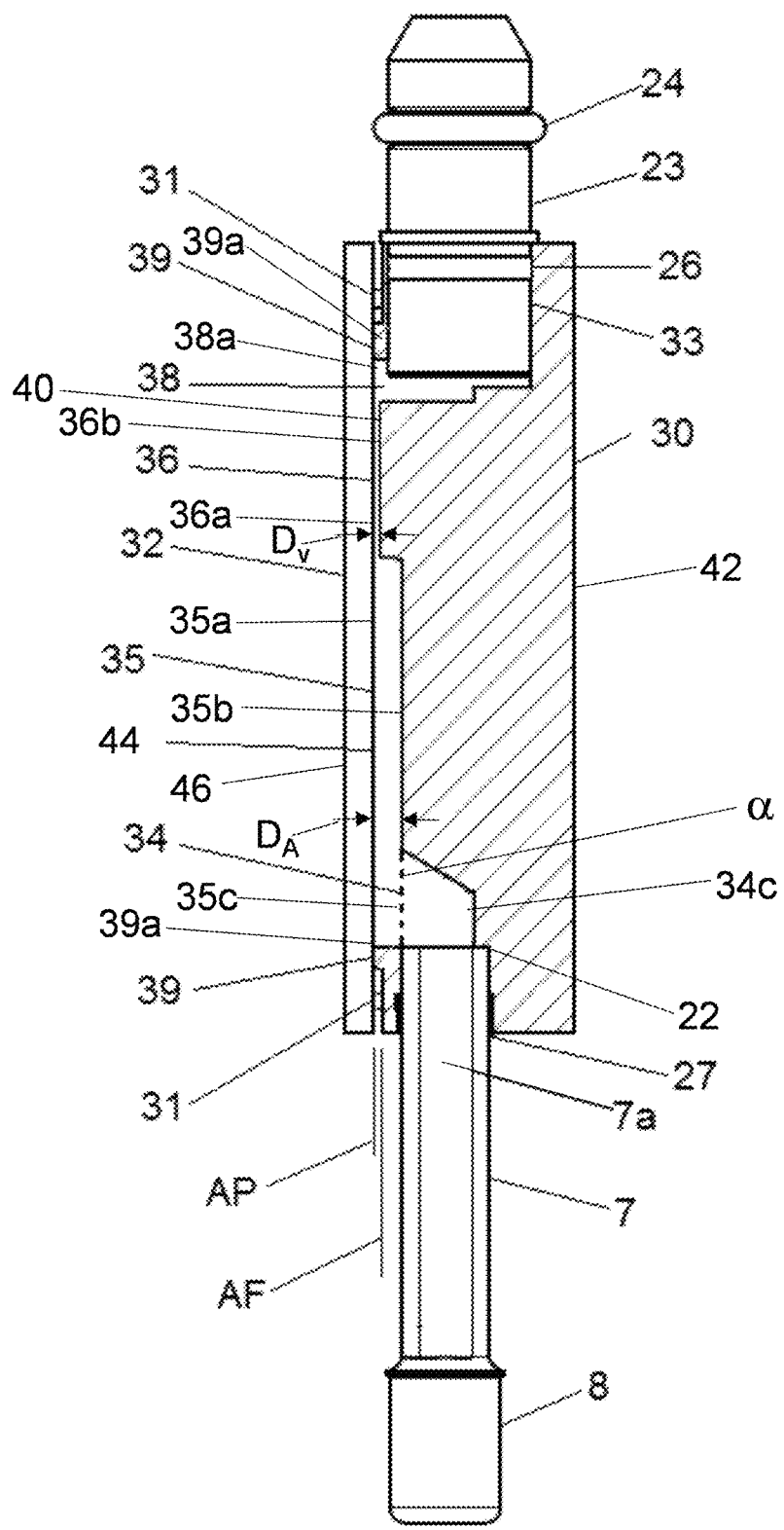
FIG. 6 is a cross-sectional side view of immersion sampling probe of FIG. 3 taken along a plane parallel to a longitudinal axis of the sample cavity.

FIGS. 4-6 show the two-part sample chamber 3 of probe 10 in greater detail. The housing 30 of the sample chamber 3 has a first side or face 40 and an opposing second side or face 42 (see FIGS. 4A and 6). The first face 40 is an analysis face, meaning it is the geometric side of the housing 30 in which the sample is collected and which is thus configured to be positioned face down upon the stage of optical emission spectrograph during analysis. The down direction, in this case, is a direction toward the spark source of an OES system. The first face 40 extends between the immersion end and the opposing end of the housing 30. More particularly, the first face 40 extends in a first plane AF from the first end 16 toward the second end 18 of the sample chamber 3. At the second end 18 of the sample chamber 3, there is provided a gas port 33 which is preferably wholly contained within the housing 30. The gas port 33 receives the coupler 2 (as shown in FIG. 1 or 3) which, as described herein, is sealed to the housing 30 in a substantially gas tight manner by the adhesive 26 (see FIG. 3).

Referring to FIGS. 4 and 6, portions of the first face 40 are hollowed out to form different regions or zones of the sample chamber 3 for ventilation and the collection of molten metal. More particularly, the first face 40 of the housing 30 includes various depressions which collectively form the sample cavity of the sample chamber 3, as follows: a first region 34 proximate the first end 16 of the sample chamber 3 and in direct communication with the inflow conduit 7, a second region 35 overlying the first region 34, a third region 36 adjacent to the second region 35. The first face 40 also includes an additional depression in the form of a fourth region 38 proximate the second end 18 of the sample chamber 3 and in direct communication with the gas port 33. The gas port 33 (and thus the coupler 2) and the inflow conduit 7 are located in the housing 30, such that they are in direct communication and aligned with the sample cavity of the sample chamber 3. More particularly, the gas port 33 and the inflow conduit 7 preferably extend parallel to the sample cavity of the sample chamber 3, and more preferably the gas port 33 and the inflow conduit 7 extends along a common longitudinal axis X of the sample cavity of the sample chamber 3.

Referring to FIG. 6, the fourth region 38 is a connecting volume defined by an indentation or depression formed in the first face 40 of the housing 30 of the sample chamber 3. The connecting volume 38 thus has an open end 38*a* at the first face 40. The connecting volume 38 is in gas communication with the gas port 33. As the molten metal generally solidifies in the third region 36, as described herein, the connecting volume 38 is generally not considered to be part of the sample housing cavity for receiving molten metal.

The third region 36 is a ventilation zone which is in gas communication with the connecting volume 38. The ventilation zone 36 is defined by an indentation or depression formed in the first face 40 of the housing 30. The ventilation zone 36 thus has an open end 36*a* at the first face 40 and an opposing closed bottom end 36*b*. A center line of the ventilation zone 36 preferably aligns with the second region 35 and the gas coupler 2.

The second region 35 is an analysis zone. The analysis zone 35 is defined by an elongated indentation or depression formed in the first face 40 of the housing 30. The analysis zone 35 thus has an open end 35*a* at the first face 40 and an opposing partially closed bottom end 35*b*. More particularly, the physical boundary of the closed bottom end 35*b* only extends across a portion of the length of the analysis zone 35.

In one embodiment, the opposing ends (i.e., the leading end and the trailing end in terms of the immersion direction I) of the analysis zone 35 are rounded for ease of machining. However, it will be understood by those skilled in the art that the ends may be any shape.

A portion of the analysis zone 35 overlays the first region 34 of the sample chamber 3. More particularly, the leading end of the analysis zone 35 (i.e., the leading end of the analysis zone 35 proximate the immersion end 16 of the sample chamber 3) overlays and is in direct communication with the first region 34 (see FIG. 6). Thus, the portion of the analysis zone 35 which overlays the first region 34 is not physically bounded by the closed bottom end 35*b*. The first region 34 is a distribution zone which is in direct communication with the inflow conduit 7. More particularly, molten metal is introduced directly into the distribution zone 34 from the second end 22 of the inflow conduit 7. As such, the inlet conduit 7 is located so as to be in direct flow communication with the distribution zone 34 in a direction parallel to the longitudinal axis X.

Again, there is no physical delineation between the analysis zone 35 and the distribution zone 34. However, these are considered separate zones in terms of the prescribed dimensions for the practice of the invention. In particular, the imaginary boundary between the analysis zone 35 and the distribution zone 34, as indicated by a dashed line 35*c* on FIG. 6, is essentially an extension of the closed bottom end 35*b*, meaning the boundary 35*c* between the analysis zone 35 and the distribution zone 34 lies in the same as the closed bottom end 35*b*. The analysis zone 35 is preferred to be of a uniform depth overlying the distribution zone 34, as discussed in greater detail herein.

Collectively, the connecting volume 38, the ventilation zone 36, the analysis zone 35 and the distribution zone 34 form the hollow volume of the sample chamber 3. The ventilation zone 36, the analysis zone 35 and the distribution zone 34 collectively comprise the cavity receiving the molten metal, meaning the sample cavity in which the molten metal (and more particularly molten steel) is introduced along the longitudinal axis X, collected, subsequently solidified to form a solidified metal sample S, and ultimately directly analyzed. The ventilation zone 36, the analysis zone 35 and the distribution zone 34 are contiguous regions.

Referring to FIGS. 4 and 6, the first face 40 of the housing 30 includes a raised portion 39 that encompasses the depressions of the connecting volume 38, the ventilation zone 36, the analysis zone 35 and the distribution zone 34. More particularly, the raised portion, herein referred to as the ridge 39, peripherally surrounds the collective volume of the connecting volume 38, the ventilation zone 36, the analysis zone 35 and the distribution zone 34. The upper or distal rim 39a of the ridge 39 is preferably at a height of 0.2 mm to 0.5 mm, and more preferably 0.3 mm, relative to the remainder of the first face 40 (i.e., relative to the first plane AF). Thus, the distal rim 39a of the peripheral ridge 39 lies in a second plane AP which is spaced apart from the first plane AF of the first face 40. The second plane AP is referred herein as the analysis plane. When the sample chamber 3 is filled with metal, the analyzable surface AS of the solidified metal sample AS lies in the analysis plane AP, as described herein in greater detail.

Figure 5A:
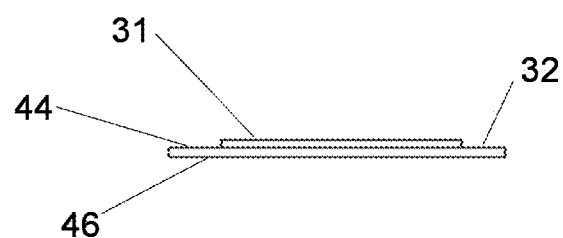
FIG. 5A is a bottom plan view of the sample chamber cover plate shown in FIG. 5.

Referring to FIGS. 5-5A, the cover plate 32 need not be formed of the same material as the housing 30. Unlike the housing 30, the cover plate 32 does not have to be formed of a material which is a good electrical conductor. For example, the cover plate 32 may be formed of fused silica or a refractory ceramic material. Preferably, however, the cover plate 32 is formed of the same material as the housing 30.

Preferably, for practical purposes of assembly, the cover plate 32 is approximately the same width and length as the housing 30. However, it will be understood that the cover plate 32 is not limited to such dimensions, and may have a width and length greater or less than that of the housing 30.

The cover plate 32 has a first side or face 44 and an opposing second side or face 46. The cover plate 32 preferably has a thickness between 1 mm and 5 mm extending from the first face 44 to the second face 46. The first face 44 of the cover plate 32 is configured to face the housing 30, and more particularly the first face 40 of the housing 30, in the assembled configuration of the sample chamber 3. A sealing member 31 is provided on the first face 44 of the cover plate 32 so as to be positioned between the housing 30 and cover plate 32 in the assembled configuration of the sample chamber 3. The sealing member 31 is preferably a gas sealing member. More particularly, the sealing member 31 is a gasket. The gasket 31 is preferably dimensioned so as to encompass or surround the ridge 39 in the assembled configuration of the sample chamber 3. The gasket 31 may be of any shape. Preferably, however, the gasket 31 is formed in the same shape as that of the ridge 39 of the first face 40 of the housing 30.

In one embodiment, the gasket 31 is preferably formed of silicone or any similar polymer. It will be understood by those skilled in the art that the gasket 31 may be formed of any material which would provide a gas tight seal between the cover plate 32 and the housing 30. After the material of the gasket 31 is applied to the first face 44 of the cover plate 32, the gasket 31 is allowed to dry before the cover plate 32 is assembled with the housing 30 and secured together by the clamp 4, thus ensuring that the gasket 31 does not adhere to the housing 30.

It will be understood by those skilled in the art that the gasket 31 may alternatively be formed as an O-ring or of a flat gasket material without departing from the scope of the invention. For example, in another embodiment, the gasket 31 is a plastic foil applied as a flat gasket preferably having a thickness of 0.04 to 0.1 mm. For example, the flat gasket may be formed of the surface protection tape, Product No. 4011a, manufactured by 3M™.

In the assembled configuration of the sample chamber 3, as shown in FIG. 6, the cover plate 32 and the housing 30 are assembled together to form the sample cavity including the distribution zone 34, the analysis zone 35 and the ventilation zone 36. Preferably, the cover plate 32 rests on the ridge 39 of the housing 30 (i.e., in the analysis plane AP) and the gasket 31 contacts the first face 40 of the housing 30 such that the gasket 31 surrounds or encompasses the ridge 39. More particularly, in the assembled configuration of the sample chamber 3, the cover plate 32 preferably sits flush against the ridge 39 in the analysis plane AP and is sealed to the first surface 40 of the housing 30 in a gasket-type fit due to the seal of the gasket 31 against the first surface 40. However, it will be understood that the cover plate 32 and the housing 30 may be assembled together along a plane that extends above the ridge 39 and the analysis plane AP.

Thus, the cover plate 32 closes the sample cavity of the sample chamber 3. Again, the sample cavity of the sample chamber 3 is the volume in which hot metal is introduced along the longitudinal axis X from the inflow conduit 7, collected and subsequently rapidly cooled to form the solidified metal sample S. As such, there are only two openings formed in the assembled sample chamber 3, namely the first opening 20 in communication with the inflow conduit 7 and the opening of the gas port 33 in communication with the coupler 2. The analysis surface of the solidified metal sample S housed with the sample cavity lies in the analysis plane AP. Further, the first opening 20 and the associated inflow conduit 7 and the gas port 33 and the associated coupler 2 are spaced apart from and do not intersect the analysis plane AP.

Hereinafter, a length L of each zone 34, 35, 36 is described in terms of a dimension parallel to and aligned with the longitudinal axis X of the sample cavity, a width W of each region 34, 35, 36 is described in terms of a dimension perpendicular to the longitudinal axis X; and a depth D of each zone 34, 35, 36 is described in terms of a dimension perpendicular to the longitudinal axis X and perpendicular to the width dimension. More particularly, a depth of each zone 34, 35, 36 is measured from a point along the analysis plane AP to the bottom end or boundary of each zone 34, 35, 36, because the sample cavity of the sample chamber 3 is bounded on one end by the zones 34, 35, 36 and on the other end by the cover plate 32 lying in the analysis plane.

Figure 11:
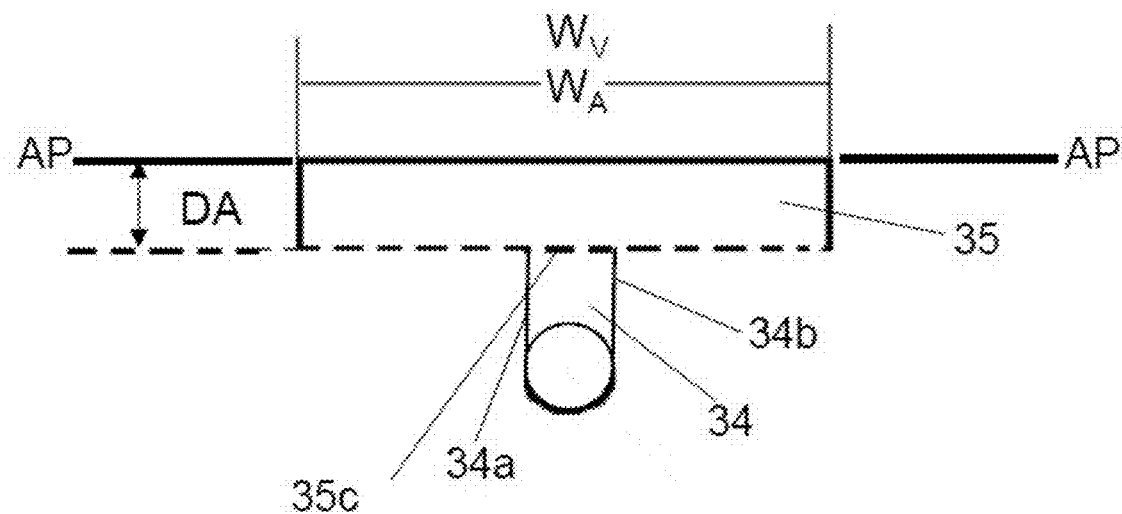
FIG. 11 is a cross-sectional view of the sample cavity of the sample chamber housing of FIG. 4 taken along a plane perpendicular to a longitudinal axis of the sample cavity.

The length L, width W and depth D dimensions are most clearly shown in FIG. 4, FIG. 6 and FIG. 11. The cross-sectional area dimension, discussed herein, is equivalent to a width W dimension multiplied by a depth D dimension (see FIG. 11).

The analysis zone 35 has a width $W_A$ of between 8 and 12 mm, preferably 10 mm. The length $L_A$ of the analysis zone 35, extending from the leading end to the trailing end (the trailing end of the analysis zone corresponding to the leading end of the ventilation zone 36) is 25 to 35 mm, preferably 30 mm. The depth $D_A$ of the analysis zone 35 extends from a point along the analysis plane AP to the closed bottom end 35b and boundary 35c (i.e., the base of the depression). The depth $D_A$ of the analysis zone 35 is greater than 1.5 mm and less than 3, preferably 2 mm. If the depth $D_A$ of the analysis zone 35 is 1.5 mm or less, then the resulting solidified steel sample S would not be homogenous as required. That is, the 1.5 mm to 3 mm depth $D_A$ of the analysis zone 35 is a critical aspect of the invention.

Figure 10:
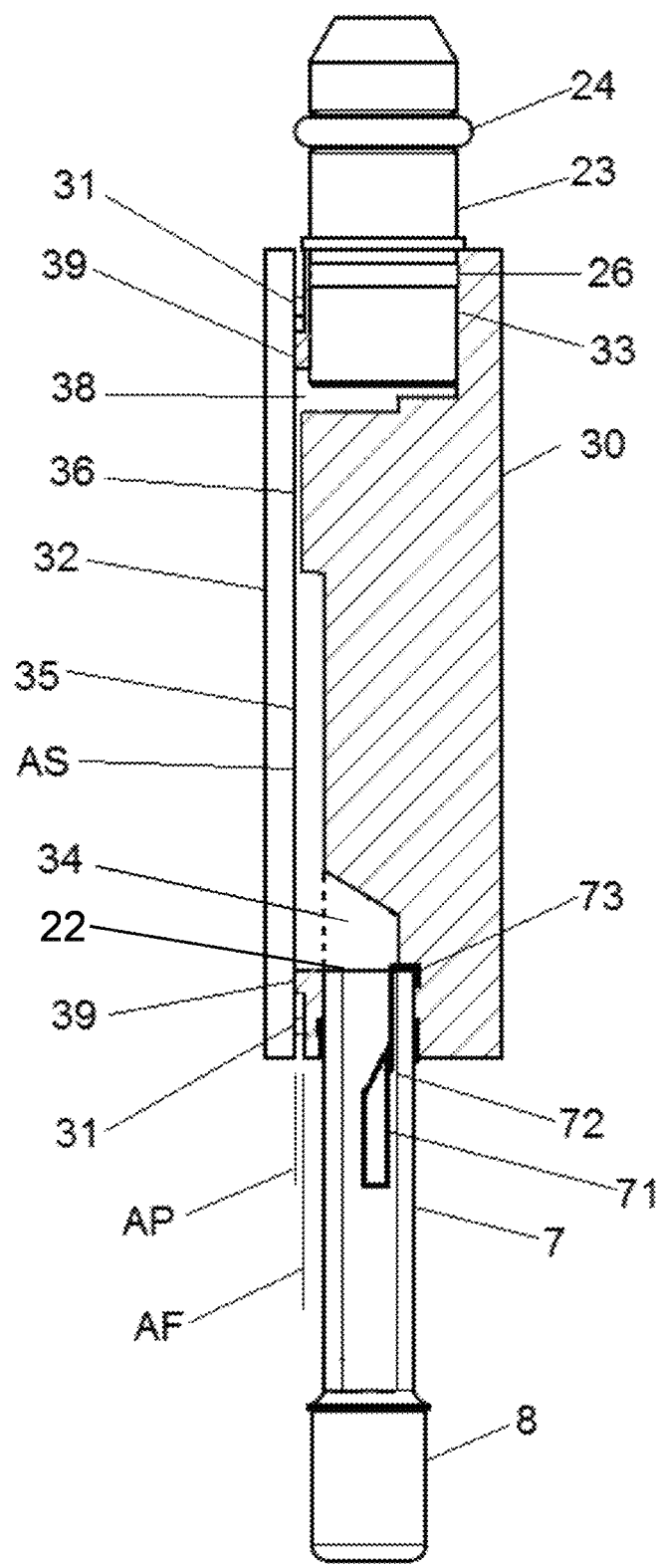
FIG. 10 is a cross-sectional side view of immersion sampling probe including a deoxidant, in accordance with another embodiment of the invention, taken along a plane parallel to a longitudinal axis of the sample cavity.

In one embodiment, the width $W_A$ of the analysis zone 35 gradually increases from proximate the immersion end 16 toward the opposing end 18 for a distance corresponding to the portion overlying the distribution zone 34. The, upon reach a maximum width $W_A$, the width $W_A$ of the analysis zone 35 tapers slightly along the longitudinal axis X, such that the cross-sectional area of the analysis zone 35 (i.e., the cross-sectional area of the analysis zone 35 taken along the plane perpendicular to the longitudinal axis X as shown in FIG. 10) is at a maximum where the distribution zone 34 ends and tapers slightly toward the ventilation zone 36. More particularly, the walls defining the width of the analysis zone 35 (i.e., the walls extending perpendicular to the first face 40) are slightly tapered in the direction of the longitudinal axis X, such that the width of the analysis zone 35 is greater at the end of the distribution zone 34 and decreases in the direction of the longitudinal axis X toward the ventilation zone 36. As such, the analysis zone 35 can accommodate shrinkage of the solidifying hot metal without undue stress on the thin cross section of the solidified metal sample S.

The cross-sectional area of the inflow conduit 7, that is the cross-section of the inflow conduit 7 taken along the plane perpendicular to the longitudinal axis X as shown in FIG. 11, is dependent upon the cross-sectional area of the analysis zone 35 and the distribution zone 34. Preferably, the cross-sectional area of the inflow conduit 7 is between 0.5 and 2 times the cross-sectional area of the analysis zone 35. More particularly, the ratio of the inflow conduit 7 to the analysis zone 35 is more than 0.5 and less than 2. Preferably, the cross-sectional area of the inflow conduit 7 is between 0.20 and 0.70 times the largest cross-sectional area of the distribution zone 34 and thus lowers the inlet velocity required for metal mixing, including for the incorporation of any deoxidants. More preferably, the cross-sectional area of the inflow conduit 7 is 0.55 times the largest cross-sectional area of the distribution zone 34. If the cross-sectional area of the inflow conduit 7 is too small (i.e., less than 0.5 times the cross-sectional area of the analysis zone 35 and/or less than 0.20 times the largest cross-sectional area of the distribution zone 34), then there is not enough deceleration of the inflowing molten metal to accomplish optimum mixing of deoxidants and reducing turbulent flow, and there is poor filling. If the cross-sectional area of the inflow conduit 7 is too large (i.e., greater than 2 times the cross-sectional area of the analysis zone 35 and/or greater than 0.70 times the largest cross-sectional area of the distribution zone 34), then the distribution zone 34, when filled, adds sensible heat to the molten metal sample that must be removed by more housing 30 mass, thus moving further from an economic solution.

The distribution zone 34, as described earlier, lies under the analysis zone 35 and therefore does not influence the overall length $L_A$ of the analysis zone 35. The volume of the distribution zone 34 is bounded by the analysis zone 35, and more particularly by the boundary 35c, on its upper end, as well as by its opposing side walls 34a, 34b and its bottom surface 34c (see FIG. 11). The side walls 34a, 34b are substantially perpendicular to the analysis plane AP. The width $W_D$ of the distribution zone 34 (i.e., the distance spanning the side walls 34a, 34b) also preferably does not exceed the width $W_A$ of the analysis zone 35 and is preferably not less than the inner diameter of the inflow conduit 7. Preferably, the width $W_D$ of the distribution zone 34 is equal to the inner diameter of the inflow conduit 7. A first portion of the bottom surface 34c (i.e., the surface opposite to the analysis zone 35) of the distribution zone 34 extends in a horizontal plane parallel to the longitudinal axis X. A second portion of the bottom surface 34c is angled, and more particularly extends upwardly at an angle α, and intersects with the closed bottom end 35b of the analysis zone 35 at an angle α between 40° and 90°, preferably 60°. The distribution zone 35 ends at this intersection. As such, the depth of the distribution zone 34 decreases in the flow direction of the molten metal from the inflow conduit 7 toward the gas coupler 2.

The depth $D_V$ of the ventilation zone 36 ranges between approximately 0.1 and 1 mm, the length $L_V$ of the ventilation zone 36 is approximately 5 mm, and the width $W_V$ of the ventilation zone 36 is preferably equal to or less than the width $W_A$ of analysis zone 35. The depth $D_V$ of the ventilation zone 36 is at its maximum at the end closer to the immersion end 16 of the sample chamber 3. That is, the depth $D_V$ of the ventilation zone 36 decreases slightly from the immersion direction I toward the connecting volume 38. More particularly, a gradual reduction in the depth $D_V$ of the ventilation zone 36 from the trailing end of the analysis zone 35 to the end of the ventilation zone 36 from 1 mm to 0.2 mm is preferred.

There are no increases in the width of the sample cavity from the end of the distribution zone to the gas coupler 2, or increases in the depth dimensions of the sample cavity in the flow direction of the molten steel from the inflow conduit 7 toward the gas coupler 2, such that metal shrinking during solidification can freely move towards the inflow conduit 7.

The cross-sectional area of the analysis zone 35 (i.e., the width $W_A$ of the analysis zone 35 multiplied by the depth $D_A$ of the analysis zone 35) is between 2.5 and 10 times the cross-sectional area of the ventilation zone 36 (i.e., the width $W_V$ of the ventilation zone 36 multiplied by the depth $D_V$ of the ventilation zone 36). Therefore, the maximum cross-sectional area of the ventilation zone 36 is between 2 and 8 mm$^2$.

Figure 8:
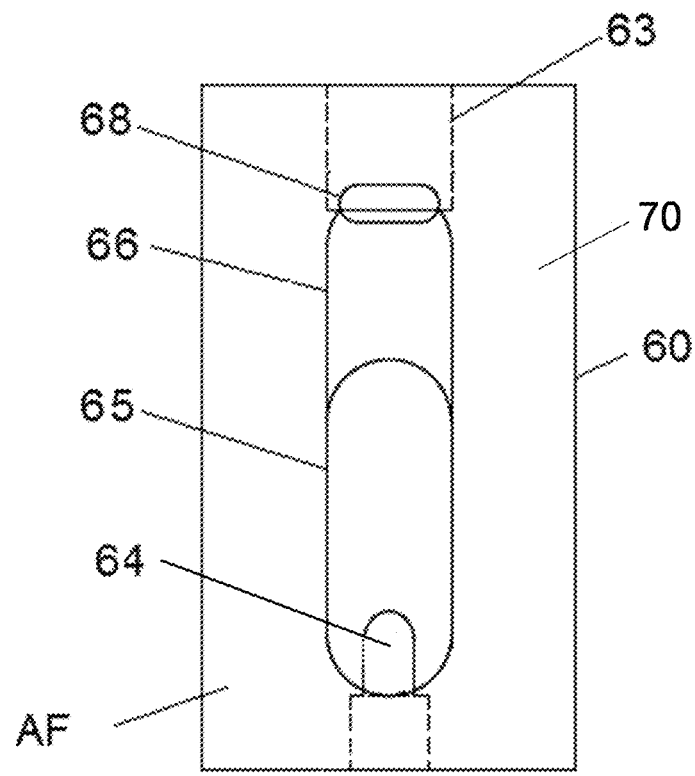
FIG. 8 is a front elevational view of the housing of a two-part sample chamber in accordance with another embodiment of the invention.
Figure 9:
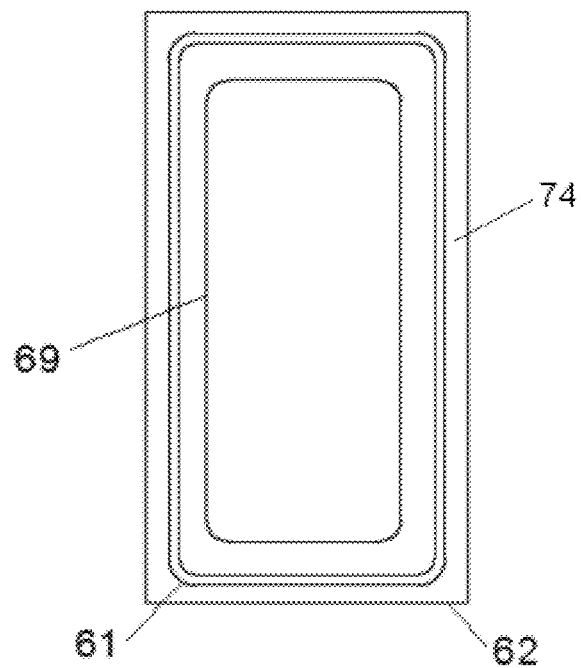
FIG. 9 is a front elevational view of the cover plate configured to be assembled with the sample chamber housing of FIGS. 8-8A.
Figure 9A:
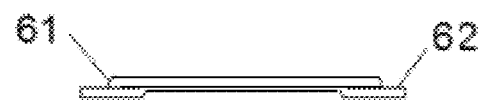
FIG. 9A is a bottom plan view of the sample chamber cover plate shown in FIG. 9.

FIGS. 8-9A show an alternative sample chamber which is essentially the same as the sample chamber 3, except for certain differences in the configurations of the housing 60 and cover plate 62, as discussed hereinafter. The housing 60 includes an connecting volume 68, a ventilation zone 66, an analysis zone 65 and a distribution zone 64 which are the same as the connecting volume 38, a ventilation zone 36, an analysis zone 35 and a distribution zone 34, respectively, of the housing 30. The housing 60 is also provided with a gas port 63 at one end, similar to the gas port 33 of the sample chamber 3, and an inflow conduit 67, similar to the inflow conduit 7 of the sample chamber 3. The housing 60 also has a first side or face 70 which is an analysis face and which extends in a first plane AF, and an opposing second face 72. Unlike the housing 30, the housing 60 does not include a raised ridge (i.e., the raised ridge 39 of the housing 30). Referring to FIGS. 9-9A, the cover plate 62 has a first face 74 configured to face the housing 60 in the assembled configuration of the sample chamber. A gasket 61 is provided on the first face 74 of the cover plate 62 so as to be positioned between the housing 60 and cover plate 62 in the assembled configuration of the sample chamber. Unlike the cover plate 32 of the sample chamber 3, the cover plate 62 further includes a raised central portion 69 extending from its first face 74. The raised central portion 69 has a height between 0.2 mm and 0.5 mm, preferably 0.3 mm. The gasket 61 surrounds or encompasses the raised central portion 69.

In the assembled configuration of the sample chamber, the raised central portion 69 of the cover plate 62 sits flush against the housing 60, with gasket 61 to sealing to the first face 70 of the housing 60. Thus, the cover plate 62 closes the open volume of the sampling chamber hollowed out from the material of the housing 60 to form the connecting volume 68, a ventilation zone 66, an analysis zone 65 and a distribution zone 64. In this embodiment, analysis plane is equal to the plane AF of the analysis face.

Referring to FIG. 10, there is shown an alternative embodiment of the sample chamber 3, 3', further including a deoxidant in the form of a strip 71. Various reference numerals utilized to describe the sample chamber 3 shown in FIG. 6 are repeated on FIG. 10, but are not repeated herein regarding the discussion of FIG. 10, as they identify the same components already described with respect to FIG. 6. The deoxidant is preferably aluminum, but may alternatively be zirconium, titanium or other such deoxidants known in the art. The width and thickness of the deoxidant strip 71 are approximately 2 mm and 0.1 mm, respectively. The deoxidant strip 71 is anchored to the inflow conduit 7 at its second end 22 opposite the immersion direction I by a bend 73 over the second end 22 of the inflow conduit 7, thereby resisting the force of the purge gas to inject the metal deoxidant strip 71 into the molten bath. The length of the metal deoxidant strip 71 is preferably as long as the length of the inlet conduit 7 that is enclosed by the measuring head 5. A portion 72 of the metal deoxidant strip 71 located in the inflow conduit 7 is preferably twisted by at least 90° in order to position its width perpendicular to the wall inflow conduit 7.

Retrieving a molten metal sample, preferably a molten steel sample, of the invention suitable for analysis using an OES from molten metal bath is accomplished by the following procedure. The probe 10 is pneumatically coupled to the probe holder with the simple push-on, pull off connector 23. The connector 23 is either directly attached to the sampling chamber 3 by the coupler 2 or at a distance joined by a pneumatic line. Closing of the gas circuit provides for a slight overpressure of inert purge gas. Using the probe holder for mechanical advantage, the probe 10 is immersed in a molten metal bath and remains at a predetermined distance beneath the metal surface for a specified duration. During this immersion, the protective cap 9 of the measuring head 5 which is designed to withstand destruction while passing through the slag floating upon the metal surface, melts away, thus exposing the smaller protective cap 8 of the inflow conduit 7. As the first protection cap 4 also subsequently melts, the overpressure of inert gas is released and the inert purge gas flows from the probe holder through the gas connector 23 (if present) and the coupler 2 into the connecting volume 38, the ventilation zone 36, the analysis zone 35, the distribution zone 34 which underlies the analysis zone 35, and the internal volume 7a of the inflow conduit. The gas connector 23 (if present) and the coupler 2 are adhered to the housing 30 in a substantially gas tight manner by adhesive 26 and the inflow conduit 7 is adhered to the housing 30 in a substantially gas tight manner by adhesive 27. More particularly, the second end 22 of the inflow conduit 7 is wholly contained within the housing 30 and adhered therein in a substantially gas tight manner by adhesive 27.

This purge gas removes the potentially oxidizing ambient atmosphere initially within the sampling chamber 3 and continues to flow for a few more seconds which allows for remnants of the second protective cap 9 and any slag that had been dragged down attached to the measuring head 5 to be flushed away. The pneumatic valves are then switched momentarily from purge to exhaust, such that the direction of the purge gas is reversed to remove the overpressure, particularly by allowing the excess pressure within the sample chamber 3 to exhaust by the reverse route as mentioned above and exit the sample chamber 3. Wth this, molten metal from the molten metal bath (not shown) enters into and fills the inflow conduit 7 and debouches from the volume 7a of the inflow conduit 7 into the distribution zone 34 of the sample chamber 3. The molten metal is then fed to the analysis zone 35 which overlies the distribution zone 34 and fills the analysis zone 35. A portion of the molten metal will continue to flow towards the coupler 2 at the second end of the sample chamber 3, thereby at least partially or even completely filling the narrow ventilation zone 36. The probe holder now moves in the opposite direction removing the filled sample chamber from the molten bath. One skilled in the art will recognize that the basic description of the probe holder and the pneumatic valves and switches necessary to carry out pneumatically assisted sampling are known in the art and not part of the present invention.

The small size of the retrieved molten steel is chilled by the housing 30 and cover plate 32, even as the measuring probe is removed from the steelmaking vessel. The rate of heat extraction from the molten sample cools the molten metal from temperatures as high as 1750° C. to 100° C. or room temperature within one minute, which essentially eliminates all external cooling required in conventional sampling and allows immediate de-molding without the potential of surface oxidation that would normally occur when exposing a hot metallic surface to an oxygen containing atmosphere.

The slight taper in the ventilation zone 36 promotes chilling of the molten metal before it reaches the gas coupler 2 and ensures that the solidified metal sample can shrink towards the analysis zone 35. More particularly, the molten metal which fills the ventilation zone 36 freezes in the ventilation zone 36 fully before reaching the connecting volume 38.

Rapid chill of the molten metal collected in the sample chamber 3 is achieved largely due to the relationship between the mass of the sample chamber 3 (i.e., the mass of the cover plate 32 plus the mass of the housing 30) and the volume of the collected molten metal which is converted to a mass. In the case of molten steel, which has an approximate molten density of 7 g/cm$^3$, the ratio of the mass of the sample chamber 3 to the mass of the molten steel collected within the sample chamber 3 (calculated based on the volume collected therein) is preferably in the range of 9 to 12, more preferably 10, in order to ensure an oxide free analysis surface AS.

Thus, while the internal voids of the analysis zone 35, ventilation zone 36 and distribution zone 34 must satisfy specific dimensional criteria, the overall dimensions of the sample chamber 3 (composed of the cover plate 2 and the housing 30) must also satisfy certain criteria to achieve the desired mass ratio of the mass of the sample chamber 3 to the mass of the molten metal collected within the sample chamber 3. One skilled in the art would understand that the overall width, depth and/or length of the housing 30 or cover plate 32 may be adjusted as necessary to increase or decrease the mass of the housing 30, without changing the internal voids necessary to create the sample cavity.

In particular, once allowances are made for the outer diameters of both the second end 22 of the inflow conduit 7 and the gas coupler 2, such that both are wholly contained within the sample housing, one or more dimensions of the housing 30 can be easily adjusted to meet the mass ratio requirement in order for the mass of the sample chamber 3 (where the cover plate 32 accounts for 10 to 20% of the mass of the sample chamber 3) to be between 9 to 12 times, preferably 10 times, the mass of the metal sample S.

Preferably, the molten metal freezes in the analysis zone 35 against the cover plate 32, and more particularly against the first surface 44 of the cover plate 32, thereby forming the analysis surface AS of the sample S which is the surface configured to be positioned face down upon the stage of optical emission spectrograph during analysis of the sample S. The analysis surface AS extends in the plane where the first face 44 of the cover plate 32 directly contacts the surface formed by the ridge 39 (i.e., the analysis plane AP). For example, in the embodiment of FIGS. 1-7A, the analysis surface AS extends in the same plane as the ridge 39 of the housing 30, namely the analysis plane AP. More particularly, both the analysis surface AS of the solidified metal sample S and the surrounding metal ridge 39 extend the analysis plane AP to help close the opening of the OES. In the embodiment of FIGS. 8-8A, discussed in greater detail herein, the analysis surface AS would extend in the plane where the raised central portion 69 of the cover plate 62 sits flush against the first face 70 of the housing 60.

When the molten metal freezes in the sample chamber 3 as such, the solidified metal sample S is formed inseparably from the housing 30. The measuring head 5 is easily fractured allowing removal of the sampling chamber 3 from the carrier tube 1 in the forward, immersion direction I. The clip 4 holding the two part sample chamber 3 is removed. Unlike conventional sampling devices, the sample S remains attached to the sample housing 30. Therefore, the term "sample", when referring herein to the metal coupon delivered to the OES, refers to the inseparable combination of the retrieved solidified sample and the sample housing 30.

The sample S is then delivered to the OES by conventional means and directly analyzed by the OES without surface preparation. The rapid chill of the sample S avoids the surface oxidation normally encountered during the de-molding step. This eliminates the need for mechanical grinding and facilities rapid analysis of the sample S and reporting the chemistry to the metal process awaiting these results. Because the inflow conduit 7 and the gas port 33 (as well as the gas coupler 2) are situated within the housing 30 spaced apart from, and more particularly below, the analysis plane (as well as below the analysis face 40), rather than straddling both sides as is normally encountered in prior art clamshell molds where these components lie along the mold parting line, it is not necessary to remove the inflow conduit 7 and the gas coupler 2 from the housing 30, in order to obtain an oxide free surface, thus allowing for the creation of a solidified metal sample that can be directly placed on an OES without preparation (i.e., preparation free analysis). That is, no part of the inflow conduit 7 and gas port 33/gas coupler 2 intersects with the analysis plane AP, such that the inflow conduit 7 and the gas port 33/gas coupler 2 do not interfere with the analysis plane AP.

The inseparability of the sample S and the housing 30 results in an extension of the housing 30 on either side of the solidified metal (i.e., by the ridge 39) along the analysis plane provides multiple improvements over the prior art. Conventional prior art samples completely cover the analysis opening of the OES, and thus have a sample size that has more material than is needed for an acceptable metal sample. During OES, the spark should not jump to the edge material of the OES sample stage, so this opening is purposefully rather large as previously described. Inert gas is purged into the spark chamber during analysis so that leaks between the sample S to be analyzed and the spectrometer stage cannot be tolerated.

The invention utilizes the inseparability of the sample S and the housing 30 to also provide a portion of the housing 30 surface for covering the analysis opening. The sampler housing 30 extending perpendicular to the elongation axis allows for an analysis zone to be just slightly larger than the burn area of the OES spark. Because of this extension of the analysis plane AP by the sampler housing 30, the volume of the molten metal filling the analysis zone 35 of the sampler housing 30 can be much smaller. This reduced volume translates to reduced heat input so that together the heat of the molten metal filling the distribution zone 34, analysis zone 35 and ventilation zone 36 is substantially less than prior art devices, and therefore can be rapidly chilled to achieve a non-segregated metal sample.

Figures 7, 7A:
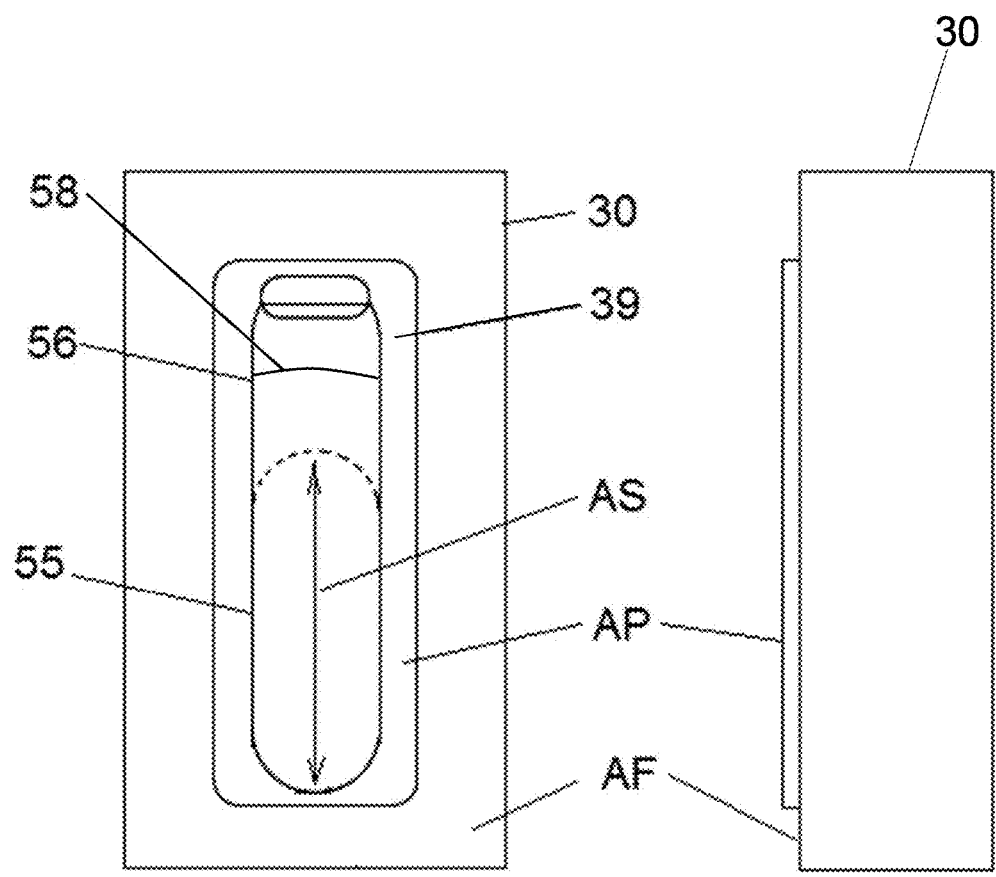
FIG. 7 is a front view of the sample chamber housing containing a solidified metal sample therein and suitable for OES analysis without preparation.
FIG. 7A is a side view of the sample chamber housing shown in FIG. 7.
Figure 8A:
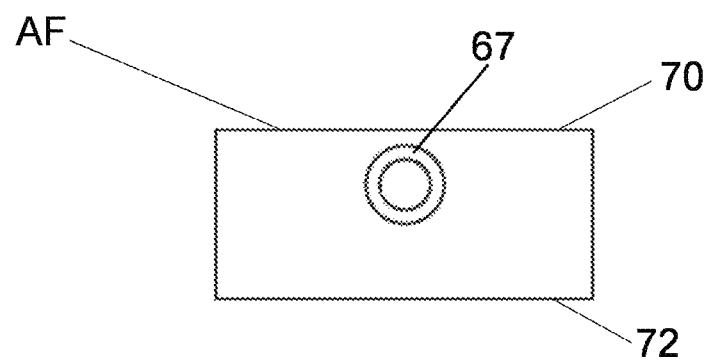
FIG. 8A is a bottom plan view of the sample chamber housing shown in FIG. 8.

Referring to FIGS. 7-7A, there is shown a disassembled sample chamber 3. More particularly, FIGS. 7-7A show the housing 30 containing a solidified metal sample S inseparably contained therein with the cover plate 32 not shown as it has been disassembled from the housing 30. The housing 30 containing the solidified metal sample S, in the form shown in FIGS. 7-7A, may be used for direct analysis by OES. The analysis surface AS comprises the surface of the portion 55 of the sample S formed in the analysis zone 35 which sits above the metal filling distribution zone 34. The remaining portion 56 of the sample S extending from and contiguous with the analysis zone portion 55 is made up of metal which has flowed into and solidified within the ventilation zone 36 and, as a last resort, possibly the connecting volume 38. Preferably, however, in order to ensure that the desired length to depth (L/D) ratio of all segments of the sample cavity is met, as discussed in greater detail herein, no molten steel flows into the connecting volume 38. The remaining portion 56 of the sample S may thus include irregularities, such as the irregular structure 58, which do not influence the subsequent OES analysis. The analysis surface AS lies in the analysis plane AP and there are no parts or extraneous adhering materials which may break the analysis plane AP.

The various zones 34, 35, 36 of the sample chamber 3, as discussed above, correspond to different portions of the solidified metal sample S formed in the sample chamber 3. As such, the dimensions of the ventilation zone 36, analysis zone 35 and distribution zone 34 correspond to the dimensions of various portions of the solidified metal sample S formed therein. For example, a depth of each of the zones 36, 35, 34 corresponds a thickness of a corresponding portion of the solidified metal sample S. In particular, the ratio of the length L to the depth D (L/D) of each zone 34, 35, 36 (and thus the corresponding ratio of the various segments of the sample S) is a critical parameter of the invention. In particular, the distribution zone 34, analysis zone 35 and ventilation zone 36 are preferably structured as a plurality of contiguous segments extending from proximate the immersion end 16 to proximate the opposing end 18. Each segment has a length to depth (L/D) ratio. The L/D ratios of the segments successively increase as the distance from the first opening 20 increases. That is, the L/D ratio of one segment is greater than the L/D ratio of an adjacent preceding segment of equal length in a direction from the immersion end 16 toward the opposing end 18. This means that the thickness of the resulting sample S decreases in this same direction from one segment to the next (i.e., in the flow direction).

With all the basic geometries of the various zones 34, 35, 36 of the sample chamber 3 being calculated as discussed above, and using economical selection of the design parameters, the critical parameter of the L/D ratio can be satisfied, knowing that at each cross section of any of the aforementioned zones or segments, the sample chamber housing 30 facilitates solidification of the metal sample S without variations (particularly increases) in the depth D dimension of the sample cavity in the direction along the longitudinal axis X beginning from the inflow conduit 7 and extending to the gas coupler 2, as well as in the thickness dimension of the sample S in the same direction.

In order to avoid crack formation in the sample S during solidification and cooling to room temperature, a summation of the L/D ratio of all segments of the sample cavity, as discussed in greater detail herein, along the total length of the sample cavity (i.e., the length $L_A$ of the analysis zone 35 plus the length $L_V$ of the ventilation zone 36), divided by the depth D of the corresponding segments (i.e., the ratio L/D) must be greater than 25. That is, the sum of the L/D ratio of each of the individual segments of the sample cavity must be greater than 25. The L/D ratio of individual segments can be selected as equally spaced segments or convened groupings as long as the total length L of the sample cavity is considered. In segment 34, where the thickness of the sample changes, i.e., the depth of the cavity changes within the segment, D is taken as the sum of the largest depth in a direction from the immersion end of the segment plus the largest depth at the end opposing the immersion end of the segment divided by 2. This calculation can be used for all segments that show depth variation over the length. Preferably, the L/D ratio of each individual segment increases in a direction from the immersion end and the inflow conduit 7 toward the gas coupler 2 (i.e., the depth of the sample cavity and correspondingly the thickness of the sample S decreases).

Figure 12:
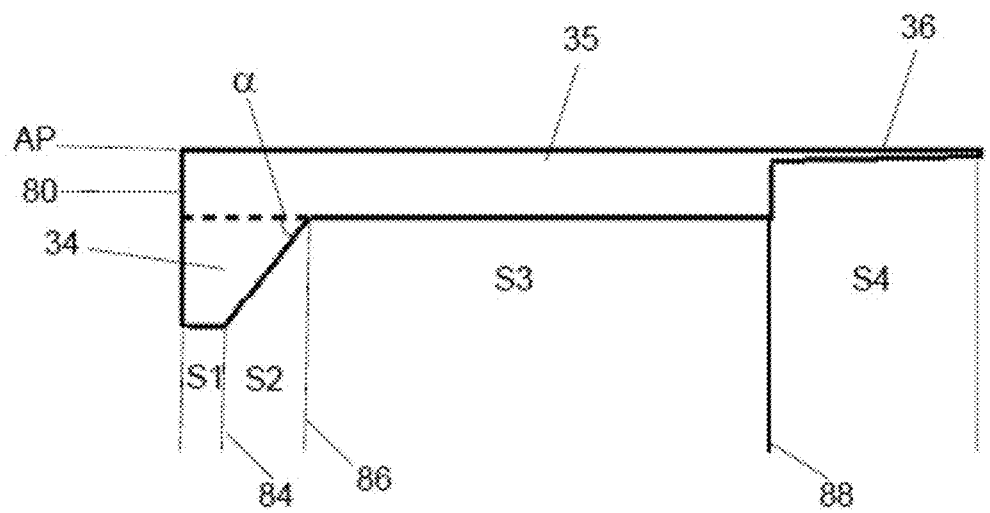
FIG. 12 is cross-sectional view, not to scale, of the sample cavity of the sample chamber housing of FIG. 4 taken along a plane parallel to a longitudinal axis of the sample cavity.

To better explain the L/D ratio, FIG. 12 shows the plurality of segments of the sample cavity including the distribution zone 34, the analysis zone 35 and the ventilation zone 36. For purposes of calculating a total L/D ratio, the sample cavity (and thus also the sample S) may be segmented as follows, but may be segmented in another manner.

A first segment S1 of the distribution zone of the sample cavity comprises a first portion of the analysis zone 35 and a first portion of the underlying distribution zone 34. The first segment S1 has a length $L_{S1}$ extending from the first end 80 of the analysis zone 35 and distribution zone 34 proximate the inflow conduit 7 to a first intermediate point 84. The first intermediate point 84 corresponds to a point in the housing 30 just before the bottom surface 34c of the distribution zone 34 begins to angle upwardly toward the ventilation zone 36. Generally, the length $L_{S1}$ of the first segment S1 is equal to or less than the diameter, and more particularly the inner diameter, of the inflow conduit 7. Other diameters can be chosen however, more preferably, the length $L_{S1}$ of the first segment S1 equals the radius of the inflow conduit 7. The depth of the first segment S1 is the sum of the depths of the corresponding portions of the analysis zone 35 and distribution zone 34 in which the first segment S1 was formed. The depth of the distribution zone 34 corresponding to the first segment S1 is measured from the boundary 35c to the horizontally-oriented bottom surface 34c, and is equal to the calculated diameter of the inflow conduit 7 plus 1 mm.

The second segment S2 of the distribution zone of the sample cavity comprises a second portion of the analysis zone 35 and a second portion of the underlying distribution zone 34. The second segment S2 has a length $L_{S2}$ extending from the first segment S1, and more particularly the first intermediate point 84, to a second intermediate point 86 which corresponds to a point in the housing 30 at which the bottom surface 34c intersects with the bottom end 35b of the analysis zone 35. Because the intersection angle is generally known (e.g., the angle is preferably 60°), the length $L_{S2}$ of the second segment S2 can be calculated. The depth of the second segment S2 is defined, as above, by the largest depth in the direction of the immersion end and the largest depth of the end opposing the immersion end of the corresponding portions of the analysis zone 35 and distribution zone 34, both divided by 2.

The third segment S3 of the sample cavity comprises the remaining portion of the analysis zone 35, and has a length $L_{S3}$ extending from the second intermediate point 86 to a third intermediate point 88 which corresponds to the end of the analysis zone 35 and the beginning of the ventilation zone 36 of the housing 30. The length $L_{s3}$ of the third segment S3 can generally be easily calculated since the overall length of the analysis zone 35 is known. The third segment S3 has a depth equal to the depth of the corresponding portion of the analysis zone 35.

The fourth segment S4 of the sample cavity comprises the ventilation zone 36. The ventilation zone 36 depth has been chosen for ease of machining, although an equally valid other depth within the range of this parameter can be chosen.

In order to create a sample housing 30 which will solidify molten steel to a crack free sample of high homogeneity according to the invention, the following examples provide exemplary configurations according to the invention, but it will be understood that many other configurations are possible within the scope of the invention.

Example 1

A sample housing 30 of aluminum is machined according to FIGS. 1-6. The analysis zone 35 has a uniform depth $D_A$ of 2 mm above the distribution zone 34. The surface area of the analysis zone 35, for Example 1, is determined from the number of analysis spots desired for OES analysis. More surface area can be provided for, however, 2-4 analysis spots are common, with 4 analysis spots being preferred. Since the typical OES analysis spot can be between 6-8 mm and it is desirable not to overlap spots, the length $L_A$ of the analysis zone 35 is chosen to be 25 mm to accommodate 3 analysis spots. It will be understood that the number of spots selected does not change the invention, as one skilled in the art can select more spots, while understanding that increasing the length of the sample S and therefore all components of the sample chamber 3 is limited only by practical consideration for the size of the spectrograph. Also, as the sample chamber 3 size increases, material costs increase, thereby leading away from providing an economic solution. Less analysis spots may also be selected, but normally 2 spots are the minimum.

The width $W_A$ of the analysis zone 35 is similarly selected to be 10 mm with a slight taper in cross section, such that the maximum cross-sectional area (i.e., depth times width) is toward the immersion direction I. Thus, the largest cross-sectional area of the analysis zone 35, which is located in the immersion direction I and more particularly proximate the inlet conduit 7, is 20 mm² (i.e., depth of 2 mm multiplied by width of 10 mm). Because the cross-sectional area of the inflow conduit 7 is between 0.5 and 2 times the cross-sectional area of the analysis zone 35, the cross-sectional area of the inflow conduit 7 of this Example can be between 10 and 40 mm$^2$. The inflow conduit 7 is a quartz tube. Therefore, the inner diameter of the inflow conduit 7 is between 3.5 and 7.1 mm. For this example, the inflow conduit 7 has an inner diameter of 4 mm (i.e., cross-sectional area of 12.6 mm$^2$). Because the cross-sectional area of the inflow conduit 7 is between 0.20 and 0.70 times the largest cross-sectional area of the distribution zone 34, the cross-sectional area of the distribution zone 34 can be between approximately 18 and 63 mm$^2$. The second portion of the bottom surface 34c of the distribution zone 34 intersects the bottom end 35b of the analysis zone 35 at an angle of 60°.

The cross-sectional area of the ventilation zone 36, at the largest area, is 2 mm$^2$. Since the width of the analysis zone 35 is 10 mm, the average depth $D_V$ of the ventilation zone 36 is 0.2 mm.

The analysis portion of a sample S created using the housing 30 of Example 1 thus has a length of 25 mm and a thickness of 2 mm (i.e., corresponding to the analysis zone 35 dimensions). The L/D ratio is first calculated for the distribution zone 34. The distribution zone 34 has a first depth from the boundary 35c of the analysis zone 35 to the horizontal bottom surface 34c of the distribution zone 34 which is equal to the calculated inflow conduit 7 inner diameter (i.e., 4 mm) plus 1 mm. This depth continues from the second end 22 of the inflow conduit 7 for a distance equal to the inner diameter of the inflow conduit 7 (i.e., 4 mm). The $L/D_1$ of the first segment S1 is the length $L_{s1}$ of the first segment S1, which is 4 mm, divided by the overall depth of the first segment S1, which is the depth of 2 mm plus 1 mm plus the inflow conduit inner diameter of 4 mm, which equals 4/7 or 0.57.

The distribution zone bottom is now slanted, preferably at 60 degrees until it intersects with the analysis zone bottom. Knowing that the intersection angle between the bottom surface 34c of the distribution zone 34 and the bottom end 35 of the analysis zone is 60°, the slanted portion of the second segment S2 will intersect the bottom of the analysis zone a distance of 2.9 mm after point 84. Therefore $L/D_2$ of the second segment S2 is the length $L_{S2}$ of the second segment, which is 2.9 mm, divided by the overall depth of the second segment S2, which is the largest depth along 84, equal to 7 plus the largest depth along 86 which is equal to 2, both divided by 2 or 9/2 for the depth of S2, and L/D of segment S2 equals 2.9/4.5 or 0.64.

The third segment S3 has a depth equal only to the depth of the analysis zone 35 (i.e., 2 mm) and a length $L_{S3}$ corresponding the remaining length for the original calculated 25 mm of the longitudinal surface of the analysis zone 35 (i.e., 25 mm-6.9 mm=18.1 mm). The $L/D_3$ of the third segment S3 is therefore 9.05.

The fourth segment S4 to calculate to design this sample housing 30 corresponds to the ventilation zone 36. The length of the fourth segment S4 (i.e., the length of the ventilation zone 36) is unknown and is determined by its conformance to the rule that the sum of L/D of all segments is greater than 25. For example, if the ventilation zone is 2 mm in length with a depth of 0.2 mm, this would result in an $L/D_4$ value of 10, and thus a summation of the L/D ratio of all of the segments of the sample S (i.e., 0.57+0.64+9.05+10) would be 20.3. As this sum is not greater than 25, it is clear that a ventilation zone 36 length of 2 mm would not be acceptable for this Example. Rather, at a minimum, a length of 3 mm is necessary for the ventilation zone 36 in order to achieve a total L/D>25. In this Example, the ventilation zone 36 length was chosen to be 5 mm and, as such, sum (L/D)=35.3 which is approximately mid-range of all economical possibilities (i.e., 25<sum(L/D)<50).

As such, it is shown that the length of each segment can be as small as measurable and still provide the necessary output. Smaller segments are desirable for the designer to conform to the criteria that no individual segment L/D can decrease in value in the direction from the inflow conduit 7 to the gas coupler 2.

Considering the requisite mass ratio of between 9 to 12, the sample chamber 3 of this Example has a housing 30 of a mass of approximately 56 g and a cover plate with a mass of approximately 9.4 g, for retrieval and chilling of a 6 g steel sample (i.e., mass ratio of 10.9).

Example 1 represents a particularly preferred embodiment of the invention.

Example 2

A sample housing 30 of aluminum is machined according to FIGS. 1-6. The analysis zone 35 has a uniform depth $D_A$ of 2 mm above the distribution zone 34. The length $L_A$ of the analysis zone 35 is chosen to be 32 mm to accommodate 4 analysis spots.

The width $W_A$ of the analysis zone 35 is similarly selected to be 10 mm with a slight taper in cross section, such that the maximum cross-sectional area (i.e., depth times width) is toward the immersion direction I. Thus, the largest cross-sectional area of the analysis zone 35, which is located in the immersion direction I and more particularly proximate the inlet conduit 7, is 20 mm$^2$ (i.e., depth of 2 mm multiplied by width of 10 mm). Because the cross-sectional area of the inflow conduit 7 is between 0.5 and 2 times the cross-sectional area of the analysis zone 35, the cross-sectional area of the inflow conduit 7 can be between 10 and 40 mm$^2$. The inflow conduit 7 is a quartz tube. Therefore, the inner diameter of the inflow conduit 7 is between 3.5 and 7.1 mm. For this example, the inflow conduit 7 has an inner diameter of 5 mm (i.e., cross-sectional area of 19.6 mm$^2$). Because the cross-sectional area of the inflow conduit 7 is between 0.20 and 0.70 times the largest cross-sectional area of the distribution zone 34, the cross-sectional area of the distribution zone 34 can be between approximately 28 and 98 mm$^2$. The second portion of the bottom surface 34c of the distribution zone 34 intersects the bottom end 35b of the analysis zone 35 at an angle of 60°.

The cross-sectional area of the ventilation zone 36, at the largest area, is 1 mm$^2$. Since the width of the analysis zone 35 is 10 mm, the average depth $D_V$ of the ventilation zone 36 is 0.2 mm.

The analysis portion of a sample S created using the housing 30 of Example 1 thus has a length of 32 mm and a thickness of 2 mm (i.e., corresponding to the analysis zone 35 dimensions). The L/D ratio is first calculated for the distribution zone 34. The distribution zone 34 has a first depth from the boundary 35c of the analysis zone 35 to the horizontal bottom surface 34c of the distribution zone 34 which is equal to the calculated inflow conduit 7 inner diameter (i.e., 5 mm) plus 1 mm. This depth continues from the second end 22 of the inflow conduit 7 for a distance equal to the inner diameter of the inflow conduit 7 (i.e., 5 mm). The $L/D_1$ of the first segment S1 is the length $L_{s1}$ of the first segment S1, which is 5 mm, divided by the overall depth of the first segment S1, which is the depth of 2 mm plus 1 mm plus the inflow conduit inner diameter of 5 mm, which equals 5/8 or 0.625.

The distribution zone bottom is now slanted, preferably at 60 degrees until it intersects with the analysis zone bottom. Knowing that the intersection angle between the bottom surface 34c of the distribution zone 34 and the bottom end 35 of the analysis zone is 60°, the slanted portion of the second segment S2 will intersect the bottom of the analysis zone a distance of 3.5 mm after point 84. Therefore $L/D_2$ of the second segment S2 is the length $L_{S2}$ of the second segment, which is 3.5 mm, divided by the largest depth at 84 which is 8 mm plus the smallest overall depth at 86 which is 2 mm both divided by 2 equals 5 mm. The L/D of S2 equals 3.5/5 or 0.7.

The third segment S3 has a depth equal only to the depth of the analysis zone 35 (i.e., 2 mm) and a length $L_{S3}$ corresponding the remaining length for the original calculated 32 mm of the longitudinal surface of the analysis zone 35 (i.e., 32 mm-8.5 mm=23.5 mm). The $L/D_3$ of the third segment S3 is therefore 11.75.

The fourth segment S4 to calculate to design this sample housing 30 corresponds to the ventilation zone 36. The length of the fourth segment S4 (i.e., the length of the ventilation zone 36) is unknown and is determined by its conformance to the rule that the sum of L/D of all segments is greater than 25. For example, if the ventilation zone is 2 mm in length with a depth of 0.2 mm, this would result in a $L/D_4$ value of 10, and thus a summation of the L/D ratio of all of the segments of the sample S (i.e., 0.625+0.7+ 11.75+10) would be 23.07. As this sum is not greater than 25, it is clear that a ventilation zone 36 length of 2 mm would not be acceptable for this Example. In this Example, the ventilation zone 36 length was chosen to be 5 mm and, as such, sum (L/D)=48 which is at the upper end of the range of all economical possibilities (i.e., 25<sum(L/D)<50).

As such, it is shown that the length of each segment can be as small as measurable and still provide the necessary output. Smaller segments are desirable for the designer to conform to the criteria that no individual segment L/D can decrease in value in the direction from the inflow conduit 7 to the gas coupler 2.

One skilled in the art can understand from the above Examples that all dimensions of the metal sample S can therefore be calculated based on the dimensions of the housing 30.

The probe 10, and particularly the sample chamber 3, could be used in all sampling applications where normal conventional sampling devices of the prior art are employed. The advantage of the present invention is best understood in light of steel processes that are very fast and overtreatment of metal and/or over processing of a heat can result in high additional expense in terms of time and materials that could have been avoided by a readily available metal chemistry at the process location.

The invention provides a solution to the shortcomings of the prior art by providing a solidified sample of steel fulfilling the following requirements:
- a metal sample that is analysed on an optical emission spectrometer,
- a solid metal sample without gas porosity and slag entrapment,
- a flat, as-retrieved analysis surface without fluid flow lines fixing the distance from the surface to the anode of the OES,
- a sample surface free of oxidation,
- a homogeneous metal sample of a maximum thickness perpendicular to the analysis plane to eliminate areas of metal and non-metallic segregation,
- a sample analytical surface spanning approximately 10 mm×30 mm and thereby providing sufficient surface area to obtain at least 2, preferably 4 sparks, and
- a sample surface that lies in the same plane as the sample housing into which the sampled metal was chilled, such that the plane of the sample analytical surface is extended without interruption in both surface directions by the sample housing 30 (namely the ridge 39) with a variation of less than 0.1 mm.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the invention as defined by the appended claims.

What is claimed is:

1. A sampler for taking samples from a molten metal bath, particularly a molten steel bath, the sampler comprising:
   a carrier tube having an immersion end;
   a sample chamber assembly arranged on the immersion end of the carrier tube, the sample chamber assembly comprising a cover plate and a housing,
   characterized in that the housing includes:
   an immersion end having a first opening for an inflow conduit and an opposing end having a second opening for a gas coupler; and
   a first face extending between the immersion end and the opposing end, the first face having a first depression proximate the immersion end and a second depression, the first depression being an analysis zone and the second depression being a ventilation zone, a portion of the analysis zone overlying a distribution zone which is in direct flow communication with the first opening and configured to receive the molten steel from the inflow conduit,
      wherein a depth of the analysis zone is greater than 1.5 mm and less than 3 mm,
      wherein the cover plate and the housing are configured to be assembled together to form a sample cavity including the distribution zone, the analysis zone and the ventilation zone, such that an analysis surface of a solidified steel sample formed within the sample cavity lies in a first plane, and
      wherein the first and second openings are spaced apart from the first plane.

2. The sampler according to claim 1, characterized in that the sample cavity and the first and second openings are aligned along a common longitudinal axis.

3. The sampler according to claim 1, characterized in that the analysis zone, distribution zone and ventilation zone are structured as a plurality of contiguous segments, each segment having a length to depth ratio, a sum of the length to depth ratios of the plurality of segments being greater than 25.

4. The sampler according to claim 1, characterized in that the distribution zone, analysis zone and ventilation zone are structured as a plurality of contiguous segments, each segment having a length to depth ratio, the length to depth ratios of the segments successively increasing as the distance from the first opening increases.

5. The sampler according to claim 1, characterized in that there are no increases in a width dimension of at least a portion of the analysis zone in a flow direction of the molten steel which extends from the end of the distribution zone toward the second opening.

6. The sampler according to claim 1, characterized in that a total length of the analysis zone and the ventilation zone is between 20 and 50 mm long.

7. The sampler according to claim 1, characterized in that the analysis zone has a uniform depth above the distribution zone.

8. The sampler according to claim 1, characterized in that a cross-sectional area of the analysis zone gradually tapers in the flow direction of the molten steel.

9. The sampler according to claim 1, characterized in that a cross-sectional area of the ventilation zone gradually tapers in the flow direction of the molten steel.

10. The sampler according to claim 1, characterized in that a ratio of a mass of the sample chamber to a mass of the metal received within the sample chamber is 9 to 12.

11. The sampler according to claim 1, characterized in that the cover plate accounts for 10 to 20 percent of the mass of the sample chamber.

12. The sampler according to claim 1, characterized in that a cross-sectional area of the inflow conduit is between 0.20 and 0.70 times of a cross-sectional area of the distribution zone.

13. The sampler according to claim 1, characterized in that a bottom surface of the distribution zone intersects a closed bottom end of the analysis zone at an angle between 40 and 90°.

14. The sampler according to claim 1, characterized in that the cover plate includes a sealing member configured to provide a substantially gas tight seal between the cover plate and the housing.

15. The sampler according to claim 1, characterized in that the cover plate is secured to the housing by a metal clamp to form the sample chamber.

16. The sampler according to claim 1, characterized in that the first and second openings are the only openings formed in the sample cavity, an end of the inflow conduit being secured within the first opening and an end of the gas coupler being secured within the second opening.

17. The sampler according to claim 1, characterized in that a cross-sectional area of the inflow conduit is between 0.5 and 2 times of a cross-sectional area of the analysis zone.

18. The sampler according to claim 1, characterized in that the inflow conduit, the distribution zone, the analysis zone, the ventilation zone and the gas coupler are sequentially arranged in this order in the flow direction of the molten steel.

19. The sampler according to claim 1, characterized in that the first face of the housing includes a ridge protruding therefrom and surrounding the ventilation zone, the analysis zone and the distribution zone.

20. The sampler according to claim 19, characterized in that when the cover plate and the housing are assembled together, the cover plate sits flush against the ridge of the housing along the first plane.

* * * * *